US008158624B2

(12) United States Patent
Castanedo et al.

(10) Patent No.: US 8,158,624 B2
(45) Date of Patent: Apr. 17, 2012

(54) PURINE PI3K INHIBITOR COMPOUNDS AND METHODS OF USE

(75) Inventors: Georgette Castanedo, Redwood City, CA (US); Irina Chuckowree, Basel (CH); Adrian Folkes, Basel (CH); Daniel P. Sutherlin, Burlingame, CA (US); Nan Chi Wan, Basel (CH)

(73) Assignee: Genetech, Inc., South San Francisco, CA (US)

( * ) Notice: Subject to any disclaimer, the term of this patent is extended or adjusted under 35 U.S.C. 154(b) by 313 days.

(21) Appl. No.: 12/474,613

(22) Filed: May 29, 2009

(65) Prior Publication Data

US 2009/0318411 A1 Dec. 24, 2009

Related U.S. Application Data

(60) Provisional application No. 61/057,559, filed on May 30, 2008.

(51) Int. Cl.
C07D 473/34 (2006.01)
A61K 31/52 (2006.01)
C07D 473/40 (2006.01)
A61P 35/00 (2006.01)

(52) U.S. Cl. .................... 514/234.2; 514/234.5; 544/81; 544/118; 544/229; 548/110

(58) Field of Classification Search ............... 514/234.2, 514/232.5; 544/81, 118, 277
See application file for complete search history.

(56) References Cited

U.S. PATENT DOCUMENTS

| 3,016,378 | A | 1/1962 | Roch |
| 4,704,381 | A | 11/1987 | Schaumann et al. |
| 4,728,644 | A | 3/1988 | Yuki et al. |
| 5,332,744 | A | 7/1994 | Chakravarty et al. |
| 5,866,702 | A | 2/1999 | Mackman et al. |
| 6,743,919 | B2 | 6/2004 | Koya et al. |
| 6,949,644 | B2 | 9/2005 | Ding et al. |
| 7,109,330 | B2 * | 9/2006 | Lum et al. ............... 544/277 |
| 7,122,665 | B2 | 10/2006 | Sun et al. |
| 7,176,312 | B2 * | 2/2007 | Ding et al. .............. 544/277 |
| 7,189,730 | B2 * | 3/2007 | Cristalli ................. 514/263.22 |
| 2003/0139427 | A1 | 7/2003 | Castelhano et al. |
| 2003/0191312 | A1 | 10/2003 | Ding et al. |
| 2005/0288503 | A1 * | 12/2005 | Adams et al. ............. 544/276 |
| 2008/0039459 | A1 | 2/2008 | Folkes et al. |
| 2008/0058297 | A1 | 3/2008 | Ono et al. |
| 2008/0207611 | A1 | 8/2008 | Shuttleworth et al. |
| 2008/0233127 | A1 * | 9/2008 | Bursavich et al. ........ 424/145.1 |
| 2010/0105705 | A1 * | 4/2010 | Eriksen et al. .......... 514/263.22 |
| 2010/0130492 | A1 * | 5/2010 | Nakayama et al. ........ 514/234.2 |
| 2010/0183564 | A1 * | 7/2010 | Boitano et al. ............ 424/93.7 |
| 2010/0305084 | A1 * | 12/2010 | Castanedo et al. .......... 514/186 |
| 2010/0305096 | A1 * | 12/2010 | Castanedo et al. ......... 514/211.15 |
| 2011/0086841 | A1 * | 4/2011 | Pei et al. ................ 514/210.21 |
| 2011/0230464 | A1 * | 9/2011 | Goldsmith et al. .......... 514/232.5 |

FOREIGN PATENT DOCUMENTS

| EP | 1 277 738 A1 | 1/2003 |
| GB | 2 431 156 A | 4/2007 |
| WO | WO 0073306 A1 * | 12/2000 |
| WO | 2004/021979 A2 | 3/2004 |
| WO | 2008/043031 A1 | 4/2008 |
| WO | 2008/116910 A1 | 10/2008 |
| WO | 2009/053716 A1 | 4/2009 |

OTHER PUBLICATIONS

Bianucci, Drug Development Research (2001), 54(2), 52-65.*
Biagi, Farmaco (2002), 57(3), 221-233.*
Bourguignon et al., "9-Benzyladenines: Potent and selective cAMP phosphodiesterase inhibitors" *J. Med. Chem.* 40:1768-1770 (1997).
Breshears et al., "Purines. VIII. Aminolysis of Certain Chlorosubstituted Purines" *J. Amer. Chem. Soc.* 81(3789-92) (1959).
Cerna et al., "Direct C-H arylation of purines: development of methodology and its use in regioselective synthesis of 2,6,8-trisubstituted purines" *Organic Letters* 8(23):5389-5392 (2006).
Ding et al., "Resin-Capture and Release Strategy toward Combinatorial Libraries of 2,6,9-Substituted Purines" *J. Comb. Chem.* 4(2):183-186 (2002).
Fiorini et al., "Solution-phase synthesis of 2,6,9-trisubstituted purines" *Tetrahedron Letters* 39(13):1827-1830 (1998).
Hammarstroem et al., "Utility of 4,6-dichloro-2-(methylthio)-5-nitropyrimidine. Part 3: Regioselective solid-phase synthesis of a 2,6,8,9-tetrasubstituted purine library" *Tetrahedron Letters* 48(16):2823-2827 (2007).
Hocek et al., "Regioselectivity in cross-coupling reactions of 2,6,8-trichloro-9-(tetrhydro-pyran-2-yl) purine: synthesis of 2,6,8-trisubstituted purine bases" *Synthesis* 17(2869-2876) (2004).
Huang et al., "Microwave-Assisted Rapid Synthesis of 2,6,9-Substituted Purines" *J. Comb. Chem.* 9(2):197-199 (2007).
Liu et al., "Parallel solution-phase synthesis of a 2,6,8,9-tetrasubstituted purine library via a sulfur intermediate" *J. Comb. Chem.* 7(4):627-636 (2005).
Vandromme et al., "Suzuki-type Pd(O) coupling reactions in the synthesis of 2-arylpurines as Cdk inhibitors" *Bioorganic & Med. Chem. Letters* 16(12):3144-3146 (2006).

(Continued)

*Primary Examiner* — Mark Berch
(74) *Attorney, Agent, or Firm* — Alex Andrus

(57) ABSTRACT

Purine compounds of Formula I, and including stereoisomers, geometric isomers, tautomers, solvates, metabolites and pharmaceutically acceptable salts thereof, are useful for inhibiting lipid kinases including p110 alpha and other isoforms of PI3K, and for treating disorders such as cancer mediated by lipid kinases. Methods of using compounds of Formula I for in vitro, in situ, and in vivo diagnosis, prevention or treatment of such disorders in mammalian cells, or associated pathological conditions, are disclosed.

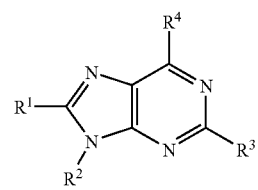

13 Claims, 2 Drawing Sheets

OTHER PUBLICATIONS

Yang et al., "Preparation of a fully substituted purine library" *J. Comb. Chem.* 7:474-482 (2005).

Sutherlin et al., "Discovery of (Thienopyrimidin-2-yl)aminopyrimidines as Potent, Selective, and Orally Available Pan-PI3-Kinase and Dual Pan-PI3-Kinase/mTOR Inhibitors for the Treatment of Cancer" Journal of Medicinal Chemistry 53(3):1086-1097 (2010).

Patent Cooperation Treaty, 'International Search Report' (International appilcation No. PCT/US2009/045603) (Sep. 21, 2009).

* cited by examiner

PURINE PI3K INHIBITOR COMPOUNDS AND METHODS OF USE

CROSS REFERENCE TO RELATED APPLICATIONS

This non-provisional application filed under 37 CFR §1.53(b), claims the benefit under 35 USC §119(e) of U.S. Provisional Application Ser. No. 61/057,559 filed on 30 May 2008, which is incorporated by reference in entirety.

FIELD OF THE INVENTION

The invention relates generally to compounds with anti-cancer activity and more specifically to compounds which inhibit PI3 kinase activity. The invention also relates to methods of using the compounds for in vitro, in situ, and in vivo diagnosis or treatment of mammalian cells, or associated pathological conditions.

BACKGROUND OF THE INVENTION

Phosphatidylinositol (hereinafter abbreviated as "PI") is one of a number of phospholipids found in cell membranes. In recent years it has become clear that PI plays an important role in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem, 274:8347-8350). The enzyme responsible for generating these phosphorylated signaling products, phosphatidylinositol 3-kinase (also referred to as PI3 kinase, PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60).

Phosphoinositide 3-kinases (PI3K) are lipid kinases that phosphorylate lipids at the 3-hydroxyl residue of the inositol ring of phosphoinositols (Whitman et al (1988) Nature, 332:664). The 3'-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

PI3 kinase is a heterodimer consisting of p85 and p110 subunits (Otsu et al (1991) Cell 65:91-104; Hiles et al (1992) Cell 70:419-29). Four distinct Class I PI3Ks have been identified, designated PI3K α (alpha), β (beta), δ (delta), and γ (gamma), each consisting of a distinct 110 kDa catalytic subunit and a regulatory subunit. More specifically, three of the catalytic subunits, i.e., p110 alpha, p110 beta and p110 delta, each interact with the same regulatory subunit, p85; whereas p110 gamma interacts with a distinct regulatory subunit, p101. The patterns of expression of each of these PI3Ks in human cells and tissues are also distinct.

The main PI3-kinase isoform in cancer is the Class I PI3-kinase, p110α (alpha) (U.S. Pat. No. 5,824,492; U.S. Pat. No. 5,846,824; U.S. Pat. No. 6,274,327). Other isoforms are implicated in cardiovascular and immune-inflammatory disease (Workman P (2004) Biochem Soc Trans 32:393-396; Patel et al (2004) Proceedings of the American Association of Cancer Research (Abstract LB-247) 95th Annual Meeting, March 27-31, Orlando, Fla., USA; Ahmadi K and Waterfield M D (2004) Encyclopedia of Biological Chemistry (Lennarz W J, Lane M D eds) Elsevier/Academic Press).

The PI3 kinase/Akt/PTEN pathway is an attractive target for cancer drug development since such agents would be expected to inhibit proliferation, reverse the repression of apoptosis and surmount resistance to cytotoxic agents in cancer cells. PI3 kinase inhibitors have been reported (Yaguchi et al (2006) Jour. of the Nat. Cancer Inst. 98(8):545-556; U.S. Pat. No. 7,173,029; U.S. Pat. No. 7,037,915; U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; U.S. Pat. No. 6,703,414; WO 97/15658; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070). Certain thienopyrimidine compounds have p110 alpha binding, PI3 kinase inhibitory activity and inhibit the growth of cancer cells (WO 2006/046031; WO 2007/122410; WO 2007/127183; WO 2007/129161; US 2008/0269210; US 2008/0242665. Certain purine compounds have p110 delta binding, PI3 kinase inhibitory activity (WO 2009/053716).

SUMMARY OF THE INVENTION

The invention relates generally to purine compounds of Formula I with anti-cancer activity, and more specifically with PI3 kinase modulating or inhibitory activity. Certain hyperproliferative disorders are characterized by the modulation of PI3 kinase function, for example by mutations or overexpression of the proteins. Accordingly, the compounds of the invention may be useful in the treatment of hyperproliferative disorders such as cancer. The compounds may inhibit tumor growth in mammals and may be useful for treating human cancer patients.

The invention also relates to methods of using the purine compounds of Formula I for in vitro, in situ, and in vivo diagnosis or treatment of mammalian cells, organisms, or associated pathological conditions.

Formula I compounds include:

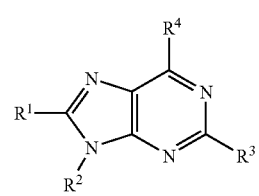

and stereoisomers, geometric isomers, tautomers, or pharmaceutically acceptable salts thereof. The various substituents $R^1$, $R^2$, $R^3$, $R^4$ are as defined herein.

Another aspect of the invention provides a pharmaceutical composition comprising a purine compound of Formula I and a pharmaceutically acceptable carrier. The pharmaceutical composition may further comprise one or more additional therapeutic agent.

Another aspect of the invention provides methods of inhibiting PI3 kinase activity, comprising contacting a PI3 kinase with an effective inhibitory amount of a compound of Formula I, or a stereoisomer, geometric isomer, tautomer, or pharmaceutically acceptable salt thereof.

Another aspect of the invention provides methods of preventing or treating a hyperproliferative disease or disorder modulated by PI3 kinases, comprising administering to a mammal in need of such treatment an effective amount of a compound of Formula I, or a stereoisomer, geometric isomer, tautomer, or pharmaceutically acceptable salt thereof. Examples of such hyperproliferative disease or disorder include, but are not limited to, cancer.

Another aspect of the invention provides methods of preventing or treating a hyperproliferative disorder, comprising administering to a mammal in need of such treatment an effective amount of a compound of Formula I, or a stereoisomer, geometric isomer, tautomer, or pharmaceutically acceptable salt thereof, alone or in combination with one or more additional compounds having anti-hyperproliferative properties.

An additional aspect of the invention is the use of a compound of this invention in the preparation of a medicament for the treatment or prevention of a disease or condition modulated by PI3 kinase in a mammal.

Another aspect of the invention includes kits comprising a compound of Formula I, or a stereoisomer, geometric isomer, tautomer, solvate, metabolite, or pharmaceutically acceptable salt thereof, a container, and optionally a package insert or label indicating a treatment.

Another aspect of the invention includes methods of preparing, methods of separating, and methods of purifying compounds of Formula I.

Another aspect of the invention includes novel intermediates useful for preparing Formula I compounds.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF EXEMPLARY EMBODIMENTS

Figure 1:
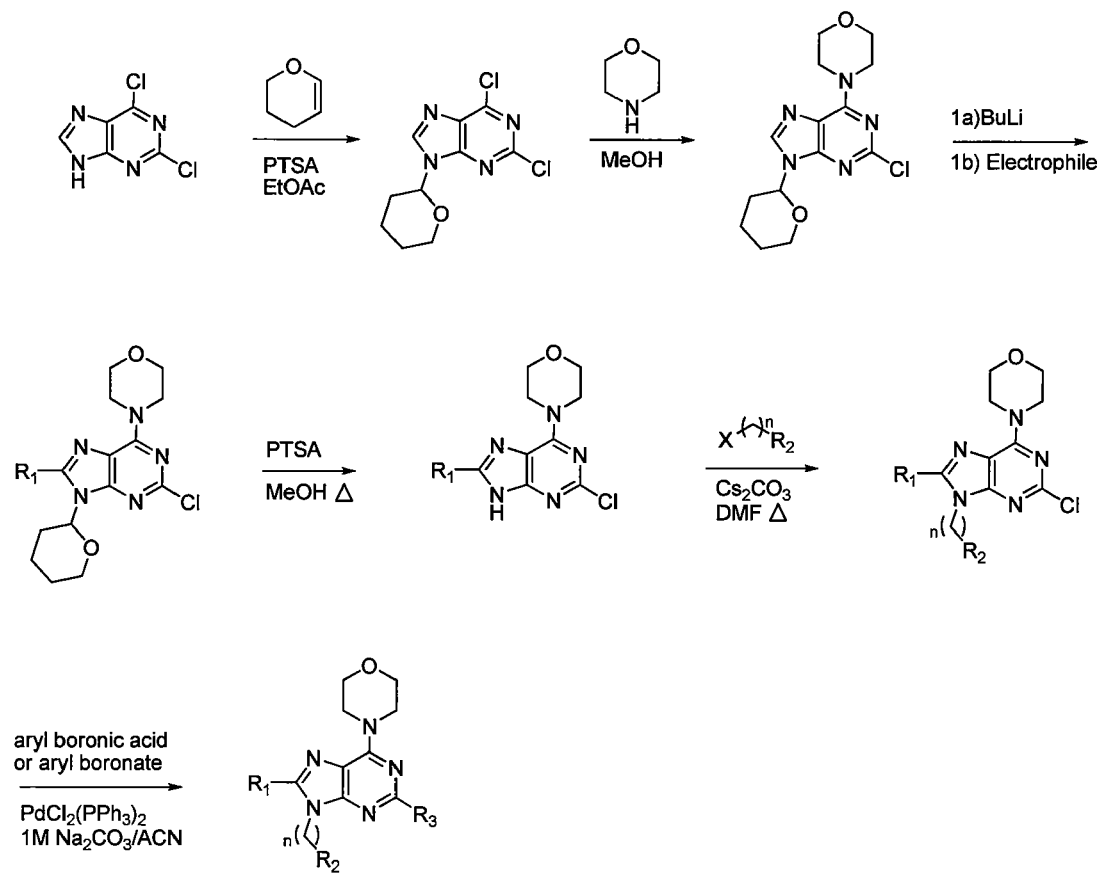
FIG. 1 shows a general method for preparation of polyfunctionalized purines

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

Definitions

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted, and includes radicals having "cis" and "trans" orientations, or alternatively, "E" and "Z" orientations. Examples include, but are not limited to, ethylenylene or vinylene (—CH=CH—), allyl (—$CH_2$CH=CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted. Examples include, but are not limited to, ethynyl (—C≡CH), propynyl (propargyl, —$CH_2$C≡CH), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynyl radical may be optionally. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted, for example, with oxo (=O), mercapto, or amino, etc. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino (piperidinyl), morpholino (morpholinyl), thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyclo[3.1.0]hexanyl, 3-azabicyclo[4.1.0]heptanyl, azabicyclo[2.2.2]hexanyl, 3H-indolyl quinolizinyl 1H-benzo[d]imidazol-2(3H)-one-5-yl, and N-pyridyl ureas. Spiro moieties are also included within the scope of this definition. Examples of a heterocyclic group substituted with one or more oxo (=O) moieties are pyrimidinonyl and 1,1-dioxo-thiomorpholinyl.

The term "heteroaryl" refers to a monovalent aromatic radical of 5-, 6-, or 7-membered rings, and includes fused ring systems (at least one of which is aromatic) of 5 to about 20 ring atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "monocyclic heteroaryl" refers to a five- or six-membered, unsubstituted or substituted, monocyclic heteroaryl radical which contains 1, 2, 3 or 4 ring heteroatoms independently selected from N, O and S. The monocyclic heteroaryl may be attached to the C-4 and C-6 positions of the pyrimidine ring according to Formula I at any carbon (carbon-linked) atom of the monocyclic heteroaryl $R^3$ group. Monocyclic heteroaryl radicals include, but are not limited to: 2-pyridyl, 3-pyridyl, 4-pyridyl, 3-isoxazolyl, 4-isoxazolyl, 5-isoxazolyl, 2-imidazolyl, 4-imidazolyl, 3-pyrazolyl, 4-pyrazolyl, 2-pyrrolyl, 3-pyrrolyl, 2-thiazolyl, 4-thiazolyl, 5-thiazolyl, 3-pyridazinyl, 4-pyridazinyl, 5-pyridazinyl, 2-pyrimidinyl, 5-pyrimidinyl, 6-pyrimidinyl, 2-pyrazinyl, 2-oxazolyl, 4-oxazolyl, 5-oxazolyl, 2-furanyl, 3-furanyl, 2-thienyl, 3-thienyl, 3-triazolyl, 1-triazolyl, 5-tetrazolyl, 1-tetrazolyl, and 2-tetrazolyl. Monocyclic heteroaryls are optionally substituted.

"Fused bicyclic $C_4$-$C_{20}$ heterocyclyl" and "Fused bicyclic $C_1$-$C_{20}$ heteroaryl" containing one or more heteroatoms independently selected from nitrogen, oxygen, and sulfur, differ only by their aromatic character, and have two rings fused together, i.e. share a common bond. Fused bicyclic heterocyclyl and heteroaryl radicals may be unsubstituted or substituted, and attached to the C-4 and C-6 positions of the pyrimidine ring according to Formula I at any carbon (carbon-linked) atom of the fused bicyclic $C_4$-$C_{20}$ heterocyclyl or fused bicyclic $C_1$-$C_{20}$ heteroaryl group $R^3$ group. Fused bicyclic heterocyclyl and heteroaryl radicals include, but are not limited to: 1H-indazole, 1H-indole, indolin-2-one, 1-(indolin-1-yl)ethanone, 1H-benzo[d][1,2,3]triazole, 1H-pyrazolo[3,4-b]pyridine, 1H-pyrazolo[3,4-d]pyrimidine, 1H-benzo[d]imidazole, 1H-benzo[d]imidazol-2(3H)-one, 1H-pyrazolo[3,4-c]pyridine, 1H-pyrrolo[2,3-c]pyridine, 3H-imidazo[4,5-c]pyridine, 7H-pyrrolo[2,3-d]pyrimidine, 7H-purine, 1H-pyrazolo[4,3-d]pyrimidine, 5H-pyrrolo[3,2-d]pyrimidine, 2-amino-1H-purin-6(9H)-one, quinoline, quinazoline, quinoxaline, isoquinoline, isoquinolin-1(2H)-one, 3,4-dihydroisoquinolin-1(2H)-one, 3,4-dihydroquinolin-2(1H)-one, quinazolin-2(1H)-one, quinoxalin-2(1H)-one, 1,8-naphthyridine, pyrido[3,4-d]pyrimidine, pyrido[3,2-b]pyrazine, benzo[d][1,3]dioxole, and 2,3-dihydrobenzo[b][1,4]dioxine.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethyl-ethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®), SU11248, Pfizer), letrozole (FEMARA®, Novartis), imatinib mesylate (GLEEVEC®, Novartis), XL-518 (MEK inhibitor, Exelixis, WO 2007/044515), ARRY-886 (MEK inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacytidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylomithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center (s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while other functional groups on the compound undergo reaction. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof Purine Compounds The present invention provides purine compounds, and pharmaceutical formulations thereof, which are potentially useful in the treatment of diseases, conditions and/or disorders modulated by PI3 kinases. More specifically, the present invention provides compounds of Formula I

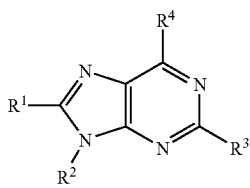

and stereoisomers, geometric isomers, tautomers, or pharmaceutically acceptable salts thereof, wherein:

$R^1$ is selected from H, $C_1$-$C_{12}$ alkyl, $C_2$-$C_8$ alkenyl, $C_2$-$C_8$ alkynyl, $C_6$-$C_{20}$ aryl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2OH$, —CN, —$CF_3$, —$CO_2H$, —$COCH_3$, —$CO_2CH_3$, —$CONH_2$, —$CONHCH_3$, —$CON(CH_3)_2$, —$NO_2$, —$NH_2$, —$NHCH_3$, —$NHCOCH_3$, —$NHS(O)_2CH_3$, —OH, —$OCH_3$, —$S(O)_2N(CH_3)_2$, —$SCH_3$, —$CH_2OCH_3$, and —$S(O)_2CH_3$;

$R^2$ is selected from $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2OH$, —CN, —$CF_3$, —$CO_2H$, —$COCH_3$, —$CO_2CH_3$, —$CONH_2$, —$CONHCH_3$, —$CON(CH_3)_2$, —$NO_2$, —$NH_2$, —$NHCH_3$, —$NHCOCH_3$, —$NHS(O)_2CH_3$, —OH, —$OCH_3$, —$S(O)_2N(CH_3)_2$, —$SCH_3$, —$CH_2OCH_3$, and —$S(O)_2CH_3$;

$R^3$ is selected from $C_6$-$C_{20}$ aryl, carbon-linked $C_2$-$C_{20}$ heterocyclyl and carbon-linked $C_1$-$C_{20}$ heteroaryl, each of which are optionally substituted with one or more groups independently selected from F, Cl, Br, I, —$CH_3$, —CN, —$CF_3$, —$CH_2OH$, —$CO_2H$, —$CONH_2$, —$CON(CH_3)_2$, —$NO_2$, —$NH_2$, —$NHCH_3$, —$NHCOCH_3$, —OH, —$OCH_3$, —SH, —NHC(=O)$NHCH_3$, —NHC(=O)$NHCH_2CH_3$, and —$S(O)_2CH_3$;

$R^4$ is selected from —$NR^{10}R^{13}$, —$NR^{12}C(=O)R^{10}$, —$NR^{10}(C_1$-$C_{12}$ alkyl)$NR^{10}R^{13}$, —$NR^{10}(C_1$-$C_{12}$ alkylene)$OR^{10}$, —$NR^{10}(C_1$-$C_{12}$ alkylene)C(=O)$NR^{10}R^{13}$, —$NR^{10}(C_1$-$C_{12}$ alkylene)-($C_3$-$C_{12}$ carbocyclyl), —$NR^{10}(C_1$-$C_{12}$ alkylene)-($C_2$-$C_{20}$ heterocyclyl), —$NR^{10}(C_1$-$C_{12}$ alkylene)-($C_6$-$C_{20}$ aryl), and —$NR^{10}(C_1$-$C_{12}$ alkylene)-($C_1$-$C_{20}$ heteroaryl), where alkyl, alkylene, carbocyclyl, heterocyclyl, aryl, and heteroaryl are optionally substituted with one or more groups independently selected from F, Cl, Br, I, —$CH_3$, —$CH_2OH$, —CN, —$CF_3$, —$CO_2H$, —$COCH_3$, —$CONH_2$, —$CONHCH_3$, —$CON(CH_3)_2$, —$NO_2$, —$NH_2$, —$NHCH_3$, —$NHCOCH_3$, —$NHS(O)_2CH_3$, —OH, —$OCH_3$, —$S(O)_2N(CH_3)_2$, —$SCH_3$, —$CH_2OCH_3$, and —$S(O)_2CH_3$;

$R^{10}$, $R^{11}$ and $R^{12}$ are independently selected from H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl, where alkyl, alkenyl, alkynyl, carbocyclyl, heterocyclyl, aryl, and heteroaryl are optionally substituted with one or more groups independently selected from F, Cl, Br, I, —$CH_2OH$, —$CH_2C_6H_5$, —CN, —$CF_3$, —$CO_2H$, —$CONH_2$, —CONHCH_3$, —$NO_2$, —$N(CH_3)_2$, —$NHCOCH_3$, —$NHS(O)_2CH_3$, —OH, —$OCH_3$, —$OCH_2CH_3$, —$S(O)_2NH_2$, —$SCH_3$, —$S(O)CH_3$, —$CH_2OCH_3$, —$CH_3$, and —$S(O)_2CH_3$;

or $R^{10}$ and $R^{11}$ together with the nitrogen atom to which they are attached form a $C_2$-$C_{20}$ heterocyclyl ring; and $R^{13}$ is selected from $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl, where alkyl, alkenyl, alkynyl, carbocyclyl, heterocyclyl, aryl, and heteroaryl are optionally substituted with one or more groups independently selected from F, Cl, Br, I, —$CH_2OH$, —$CH_2C_6H_5$, —CN, —$CF_3$, —$CO_2H$, —$CONH_2$, —$CONHCH_3$, —$NO_2$, —$N(CH_3)_2$, —$NHCOCH_3$, —$NHS(O)_2CH_3$, —OH, —$OCH_3$, —$OCH_2CH_3$, —$S(O)_2NH_2$, —$SCH_3$, —$S(O)CH_3$, —$OCH_2CH_2$—$N(CH_3)_2$, and —$S(O)_2CH_3$;

or $R^{10}$ and $R^{13}$ together with the nitrogen atom to which they are attached form a $C_2$-$C_{20}$ heterocyclyl ring;

with the proviso that when $R^1$ is —($C_1$-$C_{12}$ alkylene)-($C_2$-$C_{20}$ heterocyclyl), then $R^3$ is not an indole which is unsubstituted or substituted.

Exemplary embodiments of $R^1$ include H, $C_1$-$C_{12}$ alkyl such as $CH_3$, —$CH_2CH_3$, —$CH_2CH_2CH_3$, —$CH(CH_3)_2$, —$CH_2CH_2CH_2CH_3$, and —$CH_2CH(CH_3)_2$, $C_1$-$C_{12}$ alkyl substituted with one or more —OH or F, such as —$C(CH_3)_2$OH, —$CH_2CH_2OH$, —$CH_2CH_2CH_2OH$, and —$CH_2CH_2CO_2H$, and 2-morpholinoethyl.

Exemplary embodiments of $R^1$ also include optionally substituted phenyl.

Exemplary embodiments of $R^1$ also include —($C_1$-$C_{12}$ alkylene)-($C_2$-$C_{20}$ heterocyclyl) such as —$CH_2$-(piperazin- 1-yl) where piperazin-1-yl is optionally substituted such as —CH$_2$-(4-(methylsulfonyl)piperazin-1-yl)

Exemplary embodiments R$^2$ include C$_1$-C$_{12}$ alkyl such as CH$_3$, —CH$_2$CH$_3$, —CH$_2$CH$_2$CH$_3$, —CH(CH$_3$)$_2$, —CH$_2$CH$_2$CH$_2$CH$_3$, and —CH$_2$CH(CH$_3$)$_2$, C$_1$-C$_{12}$ alkyl substituted with one or more —OH or F, such as —C(CH$_3$)$_2$OH, —CH$_2$CH$_2$OH, —CH$_2$CH$_2$CH$_2$OH, and —CH$_2$CH$_2$CO$_2$H, and 2-morpholinoethyl.

Exemplary embodiments of R$^2$ also include —(C$_1$-C$_{12}$ alkylene)-(C$_2$-C$_{20}$ heterocyclyl) such as —CH$_2$-(piperazin-1-yl) where piperazin-1-yl is optionally substituted such as —CH$_2$-(4-(methylsulfonyl)piperazin-1-yl).

Exemplary embodiments include wherein R$^3$ is optionally substituted C$_6$-C$_{20}$ aryl. The C$_6$-C$_{20}$ aryl groups include phenyl, naphthalene, anthracene, biphenyl, indenyl, indanyl, 1,2-dihydronaphthalene, and 1,2,3,4-tetrahydronaphthyl, such as phenyl substituted with one or more —OH.

Exemplary embodiments include wherein R$^3$ is a monocyclic heteroaryl selected from pyridyl, isoxazolyl, imidazolyl, pyrazolyl, pyrrolyl, thiazolyl, pyridazinyl, pyrimidinyl, pyrazinyl, oxazolyl, oxadiazolyl, furanyl, thienyl, triazolyl, and tetrazolyl.

Exemplary embodiments include wherein R$^3$ is a monocyclic heteroaryl selected from the structures:

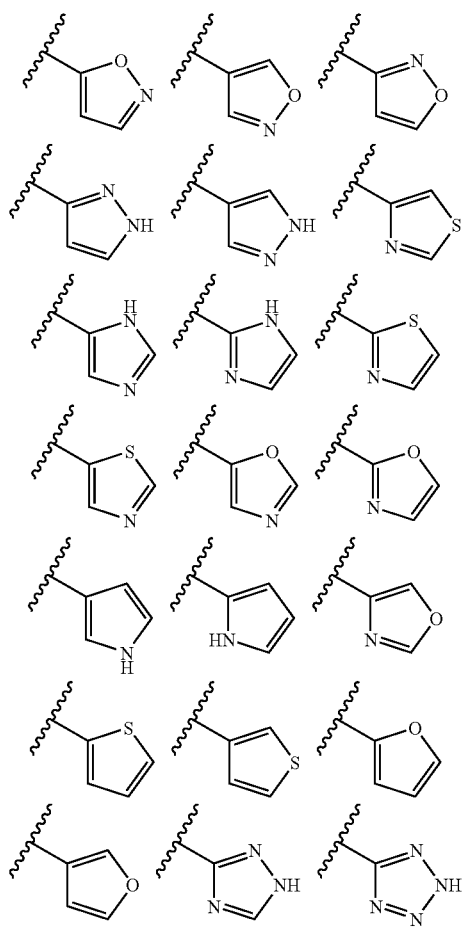

where the wavy line indicates the site of attachment.

Exemplary embodiments include wherein R$^3$ is a monocyclic heteroaryl selected from the structures:

where the wavy line indicates the site of attachment.

Exemplary embodiments include wherein R$^3$ is a monocyclic heteroaryl selected from the structures:

-continued

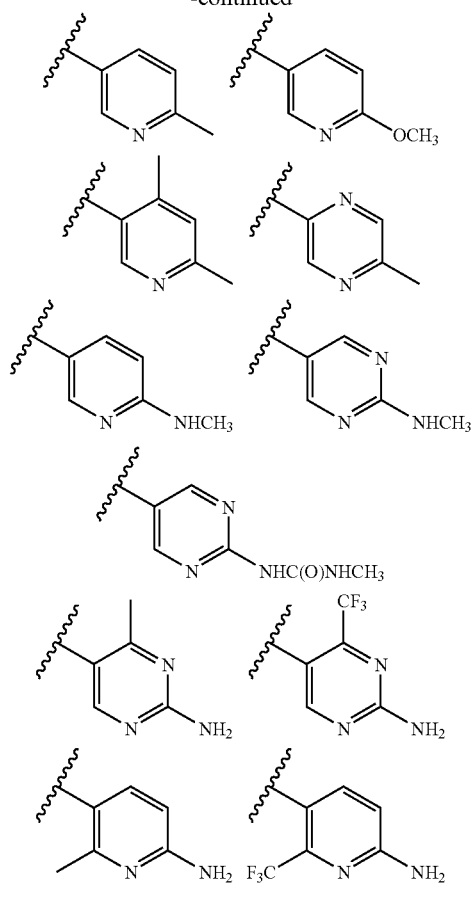

where the wavy line indicates the site of attachment.

Exemplary embodiments include wherein $R^3$ is a $C_1$-$C_{20}$ heteroaryl substituted with one or more groups selected from F, —$CF_3$, —$NH_2$, —$NHCH_3$, —OH, —$OCH_3$, —NHC(O)$CH_3$, —NHC(=O)$NHCH_3$, —NHC(=O)$NHCH_2CH_3$, —$CO_2H$, —$CH_2OH$, —C(=O)$NH_2$, and —$CH_3$.

Exemplary embodiments include wherein $R^3$ is a carbon-linked, fused bicyclic $C_4$-$C_{20}$ heterocyclyl or $C_1$-$C_{20}$ heteroaryl selected from

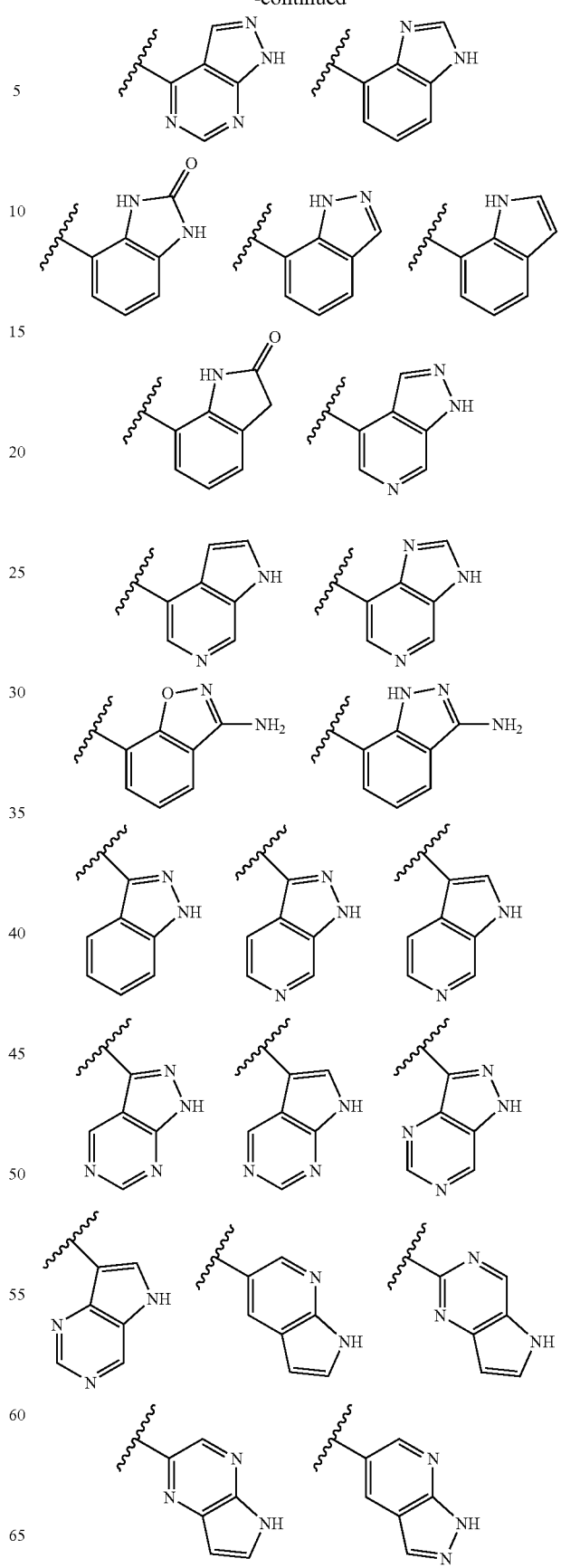

-continued

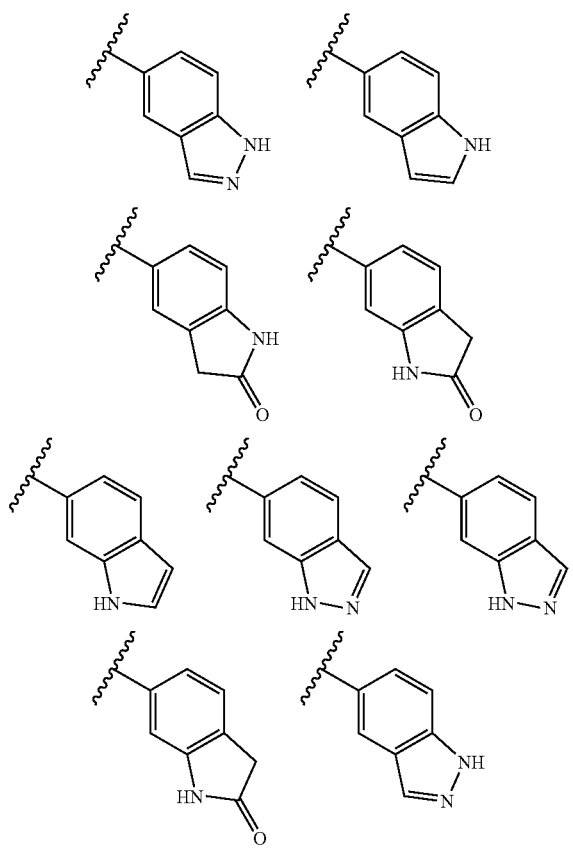

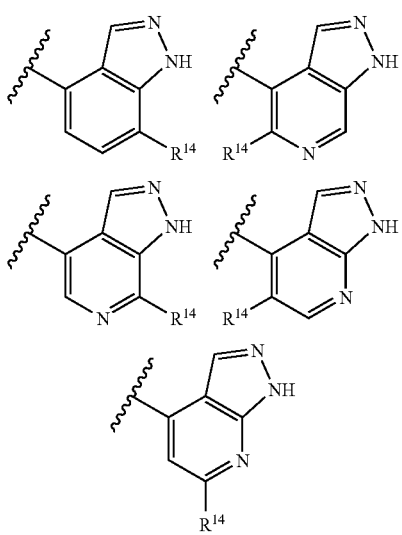

where the wavy line indicates the site of attachment.

Exemplary embodiments include wherein $R^3$ is selected from:

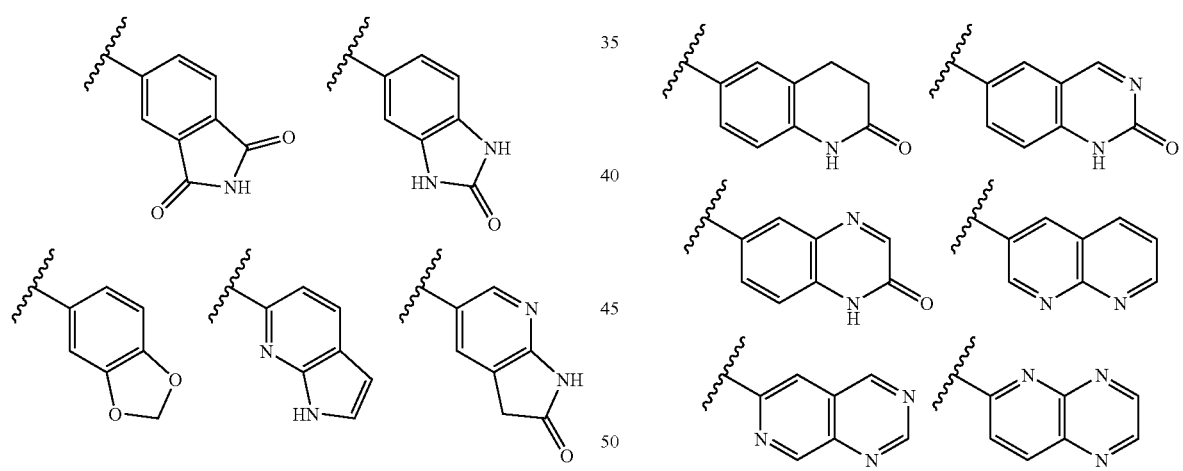

where the wavy line indicates the site of attachment and $R^{14}$ is selected from F, Cl, Br, I, —$CH_3$, —CN, —$CF_3$, —$CH_2OH$, —$CO_2H$, —$CONH_2$, —$CON(CH_3)_2$, —$NO_2$, —$NH_2$, —$NHCH_3$, —$NHCOCH_3$, —OH, —$OCH_3$, —SH, —NHC(=O)$NHCH_3$, and —S(O)$_2CH_3$.

Exemplary embodiments include wherein $R^3$ is a carbon-linked, fused bicyclic $C_4$-$C_{20}$ heterocyclyl or $C_1$-$C_{20}$ heteroaryl selected from:

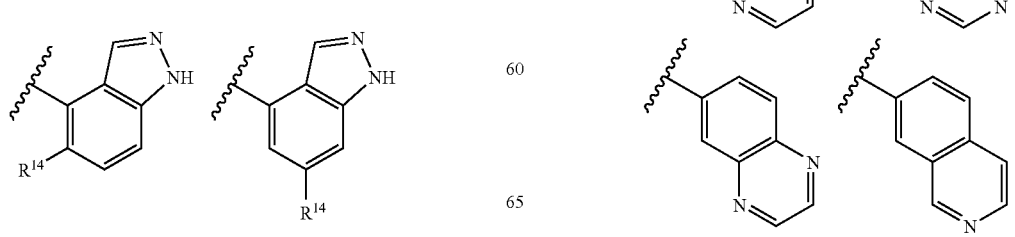

-continued

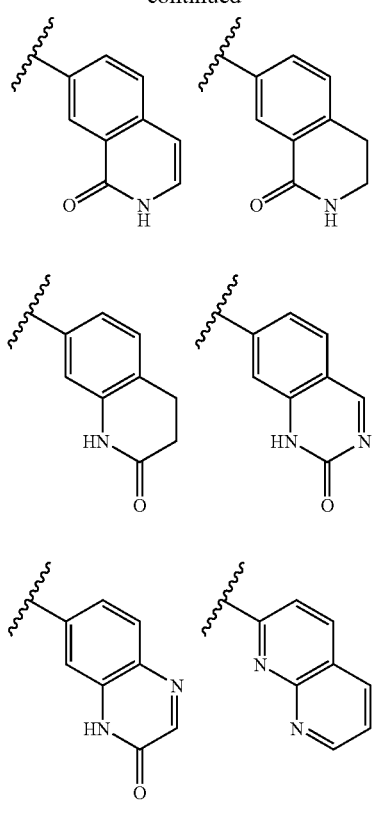

where the wavy line indicates the site of attachment.

Exemplary embodiments include wherein $R^3$ is 1H-indazol-4-yl or 1H-indol-4-yl.

Exemplary embodiments include wherein $R^4$ is —NR$^{10}$R$^{13}$ and where —NR$^{10}$R$^{13}$ form a $C_2$-$C_{20}$ heterocyclyl ring such as morpholinyl, 4-methylpiperazin-1-yl, 4-methylsulfonylpiperazin-1-yl, or 4-(2-pyridyl)piperazin-1-yl.

Exemplary embodiments include the structure:

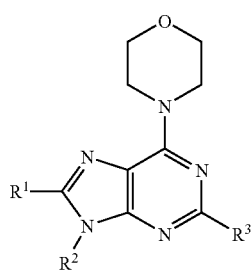

wherein $R^3$ is a monocyclic heteroaryl selected from:

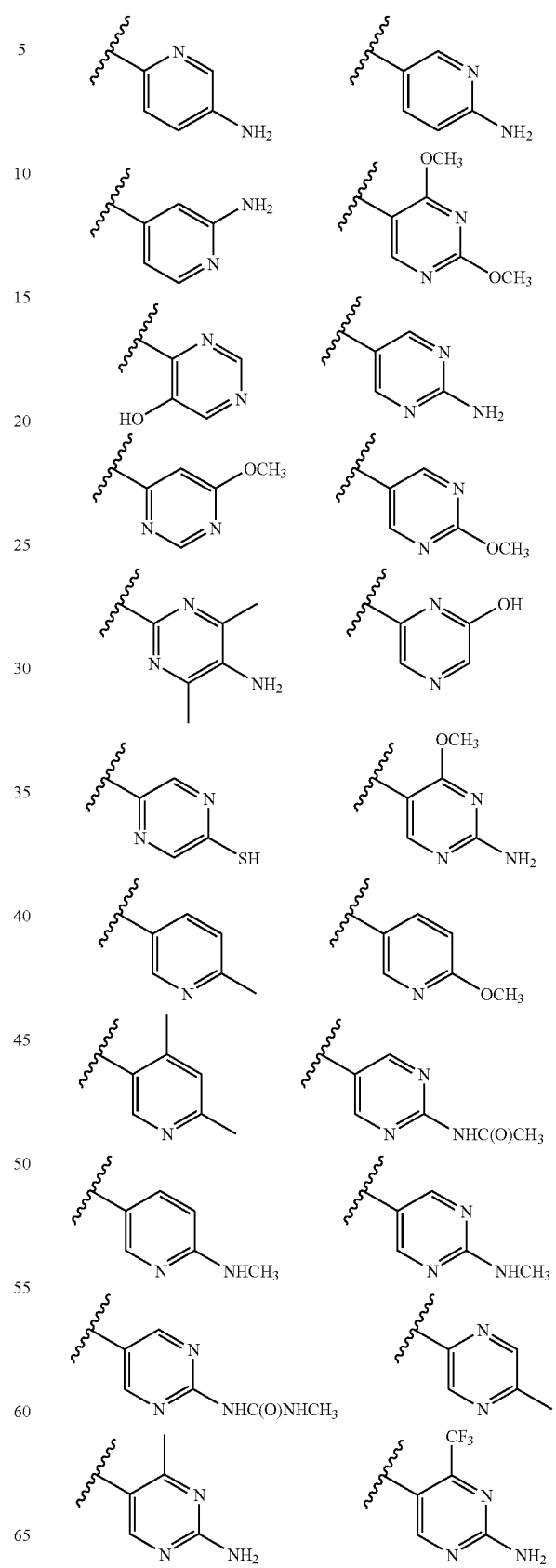

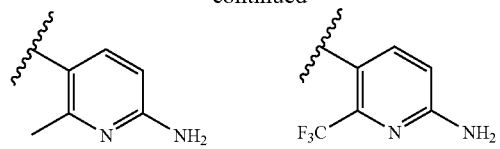

where the wavy line indicates the site of attachment, and wherein $R^1$ is selected from $C_1$-$C_{12}$ alkyl, $C_2$-$C_8$ alkenyl, $C_2$-$C_8$ alkynyl, $C_6$-$C_{20}$ aryl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2OH$, —CN, —$CF_3$, —$CO_2H$, —$COCH_3$, —$CO_2CH_3$, —$CONH_2$, —$CONHCH_3$, —$CON(CH_3)_2$, —$NO_2$, —$NH_2$, —$NHCH_3$, —$NHCOCH_3$, —$NHS(O)_2CH_3$, —OH, —$OCH_3$, —$S(O)_2N(CH_3)_2$, —$SCH_3$, —$CH_2OCH_3$, and —$S(O)_2CH_3$.

The Formula I compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all geometric and positional isomers. For example, if a Formula I compound incorporates a double bond or a fused ring, the cis- and trans-forms, as well as mixtures thereof, are embraced within the scope of the invention. Both the single positional isomers and mixture of positional isomers are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^3H$ and $^{14}C$) are useful in compound and/or substrate tissue distribution assays. Tritiated ($^3H$) and carbon-14 ($^{14}C$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Preparation of Purine Formula I Compounds

Purine compounds of Formula I may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

In certain embodiments, compounds of Formula I may be readily prepared using well-known procedures to prepare purines (Hammarstrom et al (2007) Tetrahedron Lett. 48(16): 2823-2827; Cerna et al (2006) Organic Letters 8(23):5389-5392; Chang et al (2006) J. Med. Chem. 49(10):2861-2867; Yang et al (2005) J. Comb. Chem. 7:474-482; Liu et al (2005) J. Comb. Chem. 7:627-636; Hocek et al (2004) Synthesis 17:2869-2876; Hammarstrom et al (2003) Tetrahedron Lett. 44:8361-8363; Hammarstrom et al (2002) Tetrahedron Lett. 43:8071-8073; Booth et al (1987) J. Chem. Soc, Perkin Trans. 1: Organic and Bio-Organic Chem. 7:1521-1526; Booth et al (1981) J. Chem. Soc., Chemical Communications 15:788-789; Yoneda et al (1976) J. Chem. Soc., Perkin Trans. 1: Organic and Bio-Organic Chem. 14:1547-1550; Taylor et al (1971) J. Org. Chem. 36(21):3211-3217; Lister, J. H.; Fenn, M. D. The Purines, Supplementary 1, John Wiley & Sons, 1996, Volume 54; The Chemistry of Heterocyclic Compounds, Editors Weissberger, A.; Taylor E. C., Wiley Interscience, 1971, Volume 24; Legraverend, M.; Grierson, D. S. (2006) Bioorg. Med. Chem. 14:3987-4006; Hocek, M. (2003) Eur. J. Org. Chem. 245-254;U.S. Pat. No. 7,122,665; U.S. Pat. No. 6,743,919; U.S. Pat. No. 5,332,744; U.S. Pat. No. 4,728, 644; U.S. Pat. No. 3,016,378; US 2008/0058297; US 2003/0139427; WO 2008/043031); and other heterocycles, which are described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Synthetic chemistry transformations and protecting group methodologies (protection and deprotection) useful in synthesizing purine compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, 3rd Ed., John Wiley and Sons (1999); and L. Paquette, ed., Encyclopedia of Reagents for Organic Synthesis, John Wiley and Sons (1995) and subsequent editions thereof.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

A purine compound may be prepared by using 2,4,8-trichloropurine as a starting material. The three chloro groups can be displaced by various substituents. More specifically, the most reactive chloro group (i.e., chloro at position 4) is substituted with a morpholino group to form morpholinopurine.

Figure 2:
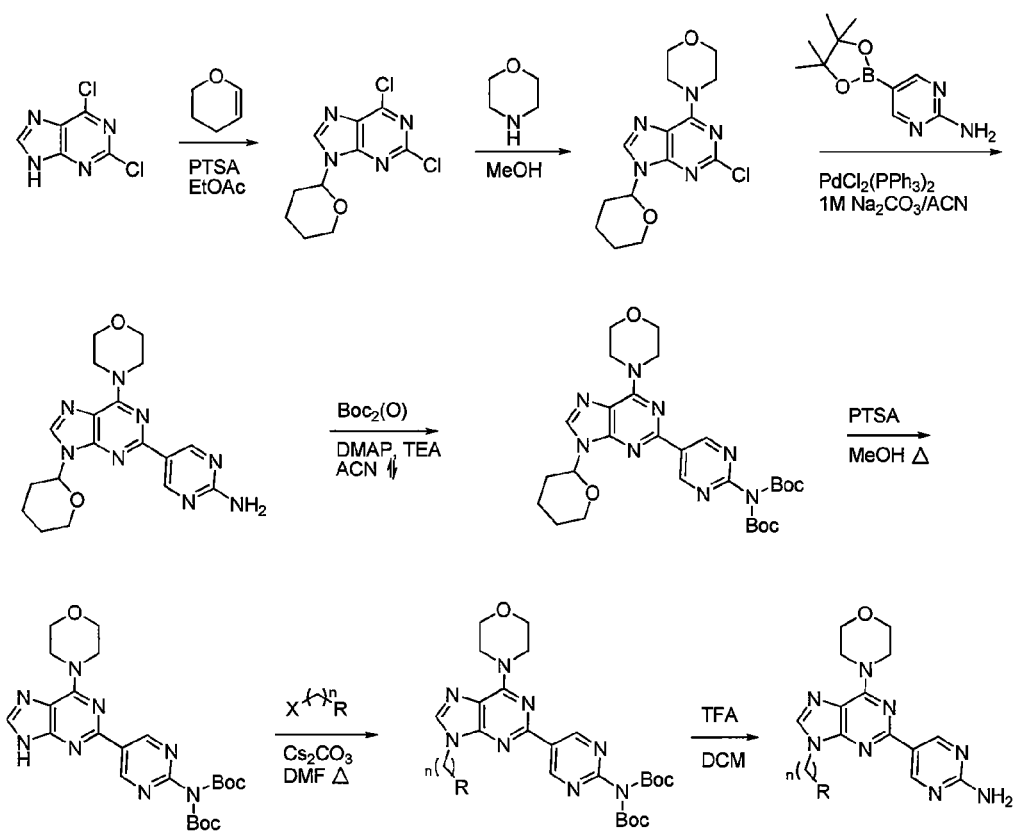
FIG. 2 shows an alternate method for the synthesis of polyfunctionalized purines.

For illustrative purposes, FIGS. 1 and 2 show general methods for preparing Formula I purine compounds, as well as key intermediates. For a more detailed description of the individual reaction steps, see the General Procedures and Examples sections. Those skilled in the art will appreciate that other synthetic routes may be used to synthesize the inventive compounds. Although specific starting materials and reagents are depicted and discussed in the Figures, General Procedures, and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

FIG. 1 shows a general method for preparation of polyfunctionalized purines starting with protection of the N-9 nitrogen of 2,6-dichloro-9H-purine as the tetrahydropyranyl group (THP). Displacement of the more reactive chloro group with morpholine gives 4-(2-chloro-9-(tetrahydro-2H-pyran-2-yl)-9H-purin-6-yl)morpholine. The C-8 proton is removed with strong base and reacted with various electrophiles ($R^1$). After deprotection with mild acid, N-9 is alkylated of N-9 with various electrophiles ($R^2$). Suzuki coupling at C-2 chloro by General Procedure A with various boronate reagents and palladium catalysts gives $C_6$-$C_{20}$ aryl, carbon-linked $C_2$-$C_{20}$ heterocyclyl and carbon-linked $C_1$-$C_{20}$ heteroaryl as $R^3$.

FIG. 2 shows an alternate method for the synthesis of polyfunctionalized purines. 2,6-Dichloro-9H-purine is protected at N-9 as THP and the more reactive chloro is displaced by morpholine to give 4-(2-chloro-9-(tetrahydro-2H-pyran-2-yl)-9H-purin-6-yl)morpholine. Suzuki coupling with 5-(4,4,5,5-tetramethyl-1,3,2-dioxaborolan-2-yl)pyrimidin-2-amine and palladium catalysis gives 5-(6-morpholino-9-(tetrahydro-2H-pyran-2-yl)-9H-purin-2-yl)pyrimidin-2-amine. Protection of the pyrimidine amine group as the bis-Boc amino and removal of THP under mild acid hydrolysis allows alkylation of N-9 with various electrophiles ($R^2$). Treatment with TFA removes the Boc groups.

Methods of Separation

In the methods of preparing the compounds of this invention, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Biological Evaluation

Determination of the activity of PI3 kinase activity of Formula I compound is possible by a number of direct and indirect detection methods. Certain exemplary compounds described herein were assayed for their PI3K binding activity (Example 52) and in vitro activity against tumor cells (Example 53). The range of PI3K binding activities was less than 1 nM (nanomolar) to about 10 µM (micromolar). Certain exemplary compounds of the invention had PI3K binding activity $IC_{50}$ values less than about 10 nM. Certain compounds of the invention had tumor cell-based activity $IC_{50}$ values less than about 100 nM.

The cytotoxic or cytostatic activity of Formula I exemplary compounds was measured by: establishing a proliferating mammalian tumor cell line in a cell culture medium, adding a Formula I compound, culturing the cells for a period from about 6 hours to about 5 days; and measuring cell viability (Example 53). Cell-based in vitro assays were used to measure viability, i.e. proliferation ($IC_{50}$), cytotoxicity ($EC_{50}$), and induction of apoptosis (caspase activation).

The in vitro potency of Formula I exemplary compounds was measured by the cell proliferation assay, CellTiter-Glo® Luminescent Cell Viability Assay, commercially available from Promega Corp., Madison, Wis. (Example 53). This homogeneous assay method is based on the recombinant expression of *Coleoptera* luciferase (U.S. Pat. No. 5,583,024; U.S. Pat. No. 5,674,713; U.S. Pat. No. 5,700,670) and determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay an be used with various multiwell formats, e.g. 96 or 384 well format. Data can be recorded by luminometer or CCD camera imaging device. The luminescence output is presented as relative light units (RLU), measured over time.

The anti-proliferative effects of Formula I exemplary compounds were measured by the CellTiter-Glo® Assay (Example 53) against several tumor cell lines, including PC3, Detroit 562, and MDAMB361.1. $EC_{50}$ values were established for the tested compounds. The range of in vitro cell potency activities was about 100 nM to about 10 µM.

Certain ADME properties were measured for certain exemplary compounds by assays including: Caco-2 Permeability (Example 54), Hepatocyte Clearance (Example 55), Cytochrome P450 Inhibition (Example 56), Cytochrome P450 Induction (Example 57), Plasma Protein Binding (Example 58), and hERG channel blockage (Example 59).

Exemplary Formula I compounds No. 101-156 in Table 1, were made, characterized, and tested for PI3K activity according to the methods of this invention, and have the following structures and corresponding names (ChemDraw Ultra, Version 9.0.1, CambridgeSoft Corp., Cambridge Mass.).

TABLE 1

| No. | Structure | Name |
|---|---|---|
| 101 | 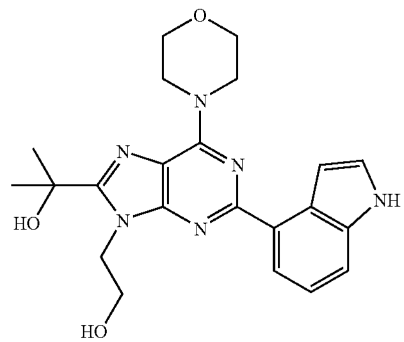 | 2-(9-(2-hydroxyethyl)-2-(1H-indol-4-yl)-6-morpholino-9H-purin-8-yl)propan-2-ol |
| 102 | 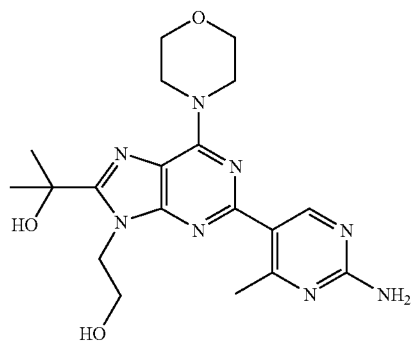 | 2-(2-(2-amino-4-methylpyrimidin-5-yl)-9-(2-hydroxyethyl)-6-morpholino-9H-purin-8-yl)propan-2-ol |
| 103 | 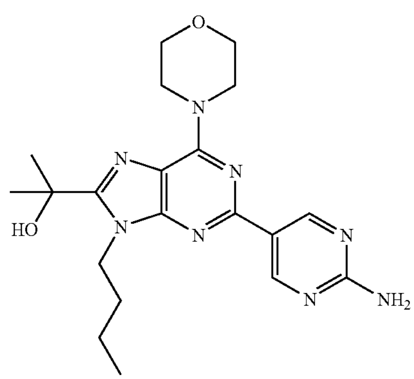 | 2-(2-(2-aminopyrimidin-5-yl)-9-butyl-6-morpholino-9H-purin-8-yl)propan-2-ol |
| 104 | 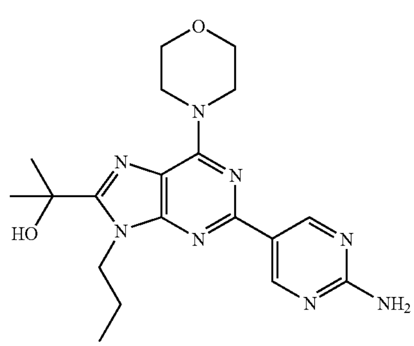 | 2-(2-(2-aminopyrimidin-5-yl)-6-morpholino-9-propyl-9H-purin-8-yl)propan-2-ol |

TABLE 1-continued

| No. | Structure | Name |
|---|---|---|
| 105 | 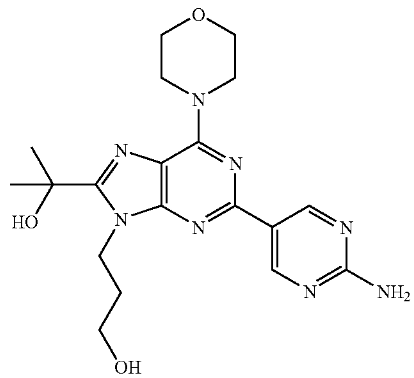 | 3-(2-(2-aminopyrimidin-5-yl)-8-(2-hydroxypropan-2-yl)-6-morpholino-9H-purin-9-yl)propan-1-ol |
| 106 | 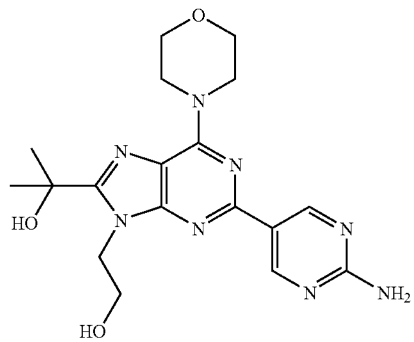 | 2-(2-(2-aminopyrimidin-5-yl)-9-(2-hydroxyethyl)-6-morpholino-9H-purin-8-yl)propan-2-ol |
| 107 | 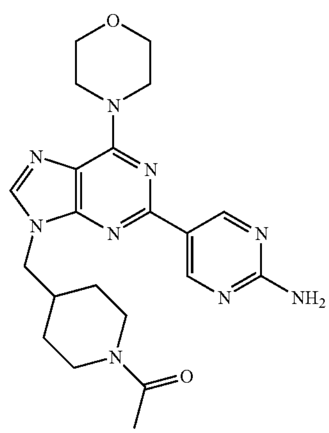 | 1-(4-((2-(2-aminopyrimidin-5-yl)-6-morpholino-9H-purin-9-yl)methyl)piperidin-1-yl)ethanone |
| 108 | 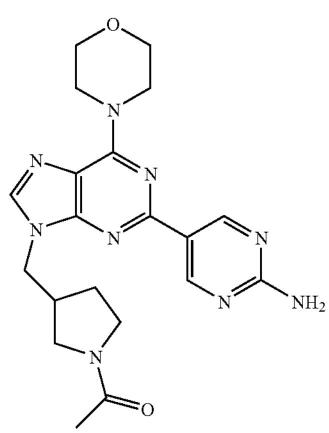 | 1-(3-((2-(2-aminopyrimidin-5-yl)-6-morpholino-9H-purin-9-yl)methyl)pyrrolidin-1-yl)ethanone |

TABLE 1-continued
| No. | Structure | Name |
|---|---|---|
| 109 | 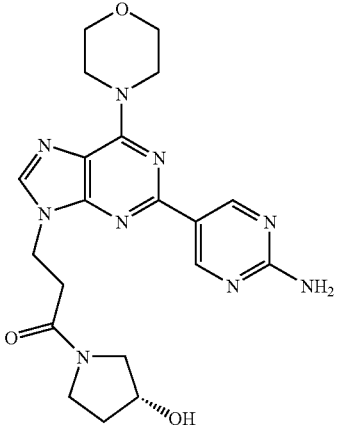 | (R)-3-(2-(2-aminopyrimidin-5-yl)-6-morpholino-9H-purin-9-yl)-1-(3-hydroxypyrrolidin-1-yl)propan-1-one |
| 110 | 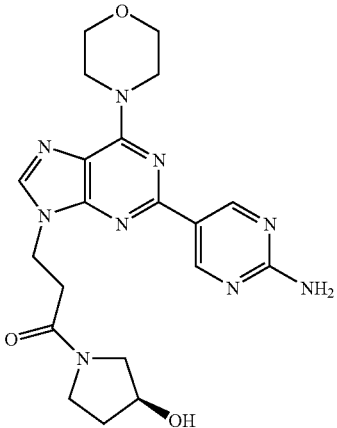 | (S)-3-(2-(2-aminopyrimidin-5-yl)-6-morpholino-9H-purin-9-yl)-1-(3-hydroxypyrrolidin-1-yl)propan-1-one |
| 111 | 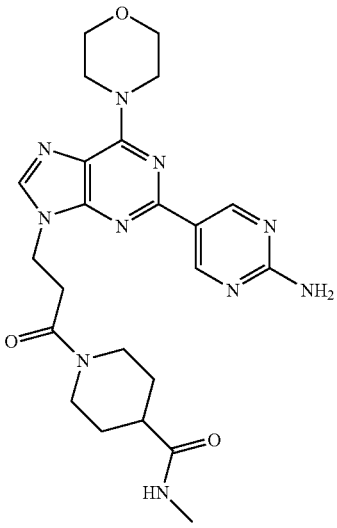 | 1-(3-(2-(2-aminopyrimidin-5-yl)-6-morpholino-9H-purin-9-yl)propanoyl)-N-methylpiperidine-4-carboxamide |

TABLE 1-continued
| No. | Structure | Name |
|---|---|---|
| 112 | 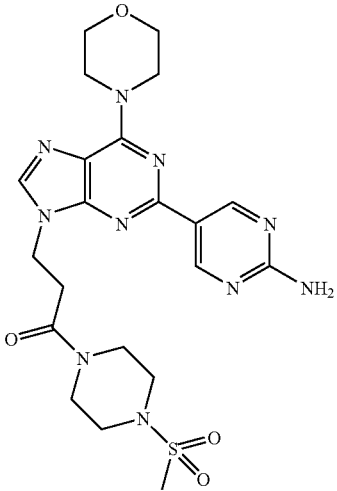 | 3-(2-(2-aminopyrimidin-5-yl)-6-morpholino-9H-purin-9-yl)-1-(4-(methylsulfonyl)piperazin-1-yl)propan-1-one |
| 113 | 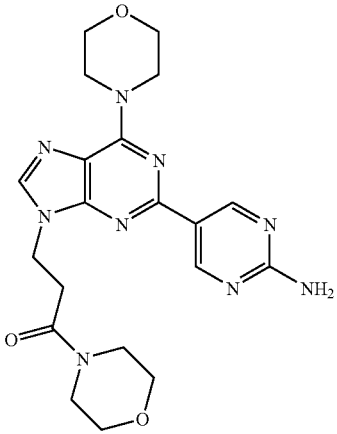 | 3-(2-(2-aminopyrimidin-5-yl)-6-morpholino-9H-purin-9-yl)-1-morpholinopropan-1-one |
| 114 | 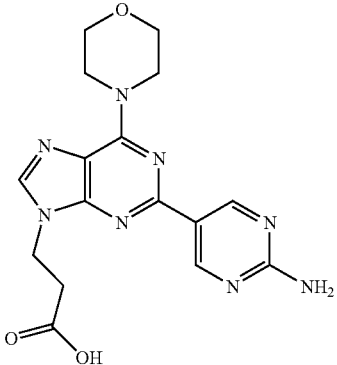 | 3-(2-(2-aminopyrimidin-5-yl)-6-morpholino-9H-purin-9-yl)propanoic acid |

TABLE 1-continued

| No. | Structure | Name |
|---|---|---|
| 115 | 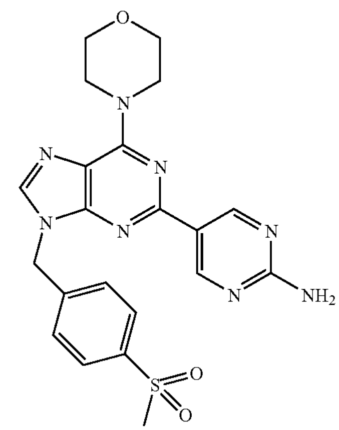 | 5-(9-(4-(methylsulfonyl)benzyl)-6-morpholino-9H-purin-2-yl)pyrimidin-2-amine |
| 116 | 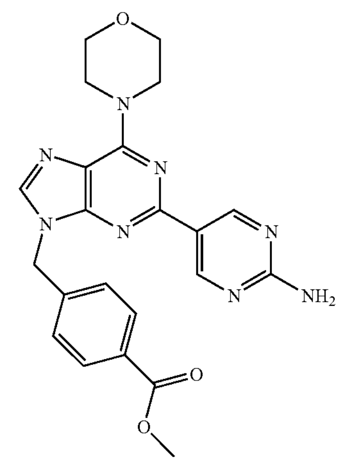 | methyl 4-((2-(2-aminopyrimidin-5-yl)-6-morpholino-9H-purin-9-yl)methyl)benzoate |
| 117 | 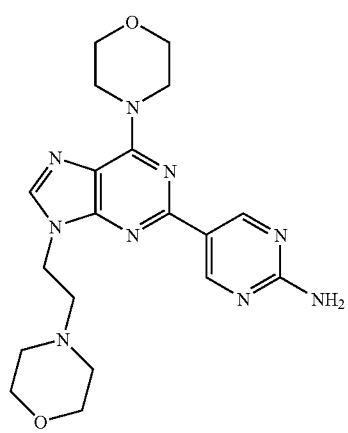 | 5-(6-morpholino-9-(2-morpholinoethyl)-9H-purin-2-yl)pyrimidin-2-amine |

TABLE 1-continued

| No. | Structure | Name |
|---|---|---|
| 118 | 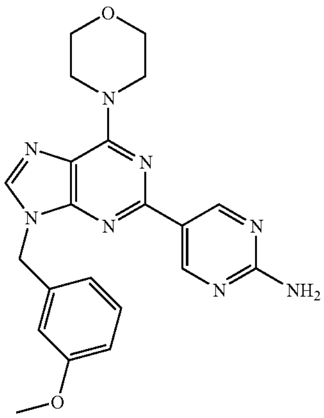 | 5-(9-(3-methoxybenzyl)-6-morpholino-9H-purin-2-yl)pyrimidin-2-amine |
| 119 | 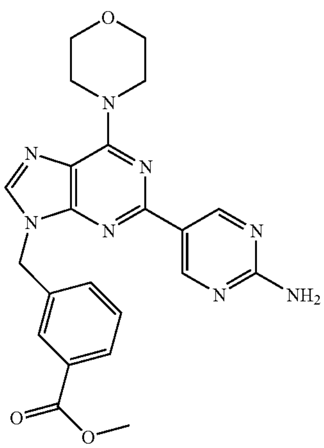 | methyl 3-((2-(2-aminopyrimidin-5-yl)-6-morpholino-9H-purin-9-yl)methyl)benzoate |
| 120 | 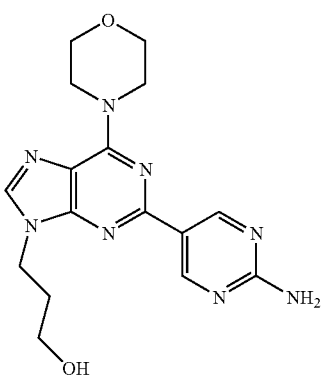 | 3-(2-(2-aminopyrimidin-5-yl)-6-morpholino-9H-purin-9-yl)propan-1-ol |
| 121 | 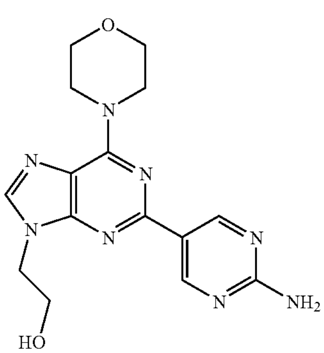 | 2-(2-(2-aminopyrimidin-5-yl)-6-morpholino-9H-purin-9-yl)ethanol |

TABLE 1-continued

| No. | Structure | Name |
| --- | --- | --- |
| 122 | 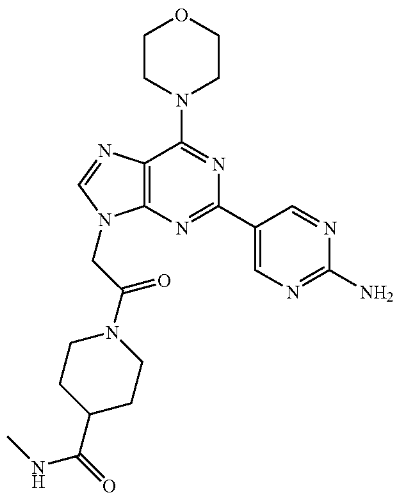 | 1-(2-(2-(2-aminopyrimidin-5-yl)-6-morpholino-9H-purin-9-yl)acetyl)-N-methylpiperidine-4-carboxamide |
| 123 | 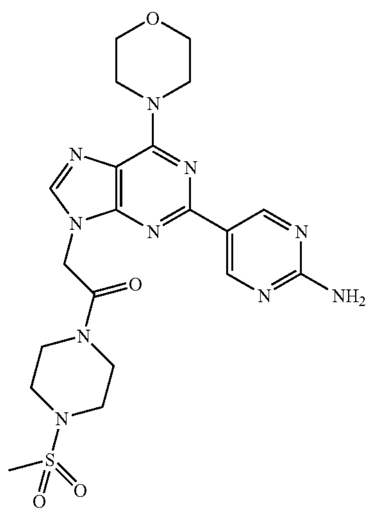 | 2-(2-(2-aminopyrimidin-5-yl)-6-morpholino-9H-purin-9-yl)-1-(4-(methylsulfonyl)piperazin-1-yl)ethanone |
| 124 | 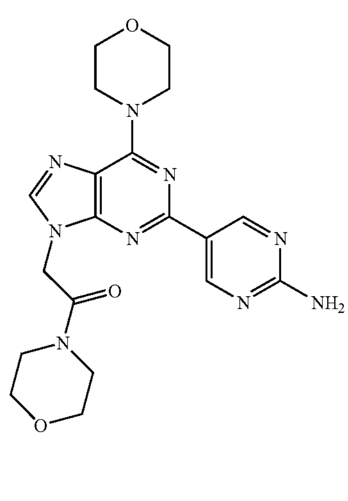 | 2-(2-(2-aminopyrimidin-5-yl)-6-morpholino-9H-purin-9-yl)-1-morpholinoethanone |

TABLE 1-continued
| No. | Structure | Name |
|---|---|---|
| 125 | 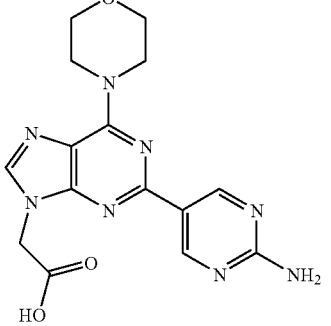 | 2-(2-(2-aminopyrimidin-5-yl)-6-morpholino-9H-purin-9-yl)acetic acid |
| 126 | 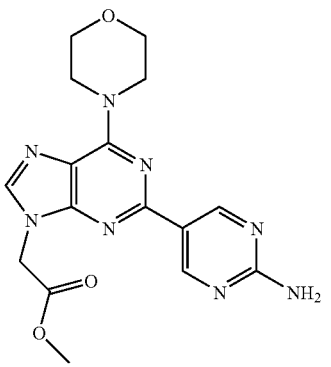 | methyl 2-(2-(2-aminopyrimidin-5-yl)-6-morpholino-9H-purin-9-yl)acetate |
| 127 | 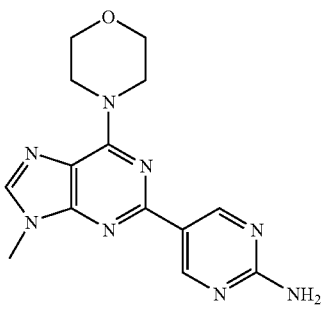 | 5-(9-methyl-6-morpholino-9H-purin-2-yl)pyrimidin-2-amine |
| 128 | 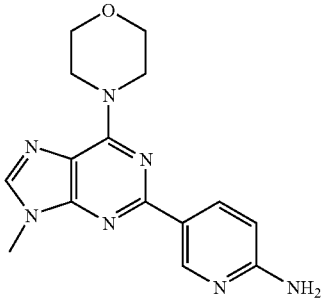 | 5-(9-methyl-6-morpholino-9H-purin-2-yl)pyridin-2-amine |

TABLE 1-continued
| No. | Structure | Name |
|---|---|---|
| 129 | 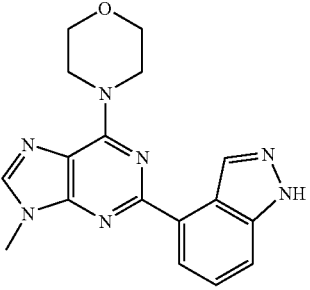 | 4-(2-(1H-indazol-4-yl)-9-methyl-9H-purin-6-yl)morpholine |
| 130 | 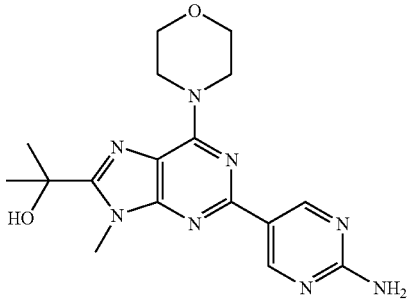 | 2-(2-(2-aminopyrimidin-5-yl)-9-methyl-6-morpholino-9H-purin-8-yl)propan-2-ol |
| 131 | 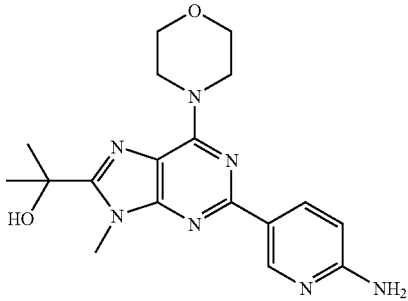 | 2-(2-(6-aminopyridin-3-yl)-9-methyl-6-morpholino-9H-purin-8-yl)propan-2-ol |
| 132 | 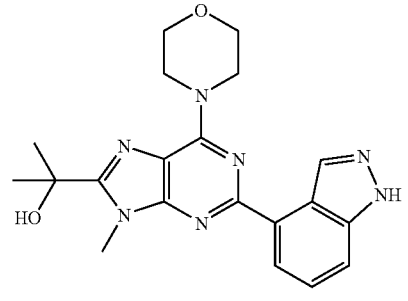 | 2-(2-(1H-indazol-4-yl)-9-methyl-6-morpholino-9H-purin-8-yl)propan-2-ol |
| 133 | 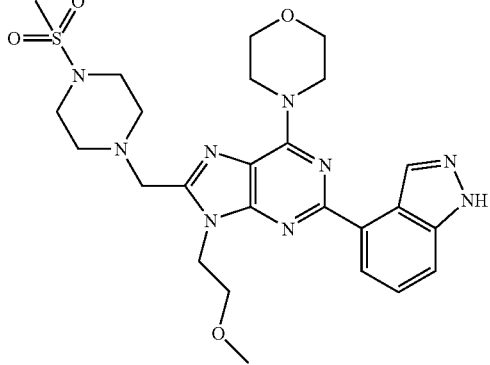 | 4-(2-(1H-indazol-4-yl)-9-(2-methoxyethyl)-8-((4-(methylsulfonyl)piperazin-1-yl)methyl)-9H-purin-6-yl)morpholine |

TABLE 1-continued

| No. | Structure | Name |
|---|---|---|
| 134 | 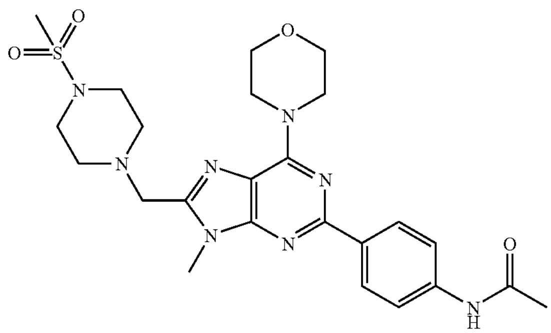 | N-(4-(9-methyl-8-((4-(methylsulfonyl)piperazin-1-yl)methyl)-6-morpholino-9H-purin-2-yl)phenyl)acetamide |
| 135 | 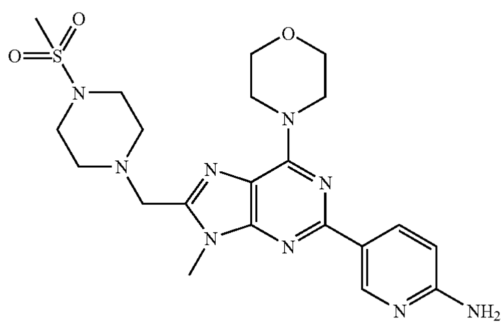 | 5-(9-methyl-8-((4-(methylsulfonyl)piperazin-1-yl)methyl)-6-morpholino-9H-purin-2-yl)pyridin-2-amine |
| 136 | 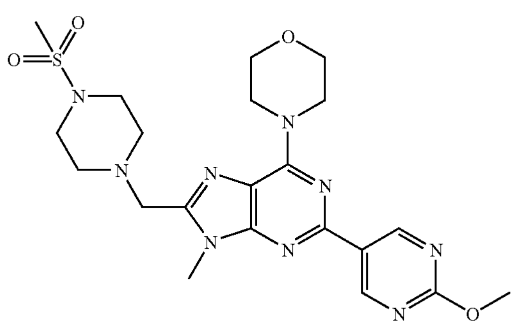 | 4-(2-(2-methoxypyrimidin-5-yl)-9-methyl-8-((4-(methylsulfonyl)piperazin-1-yl)methyl)-9H-purin-6-yl)morpholin |
| 137 | 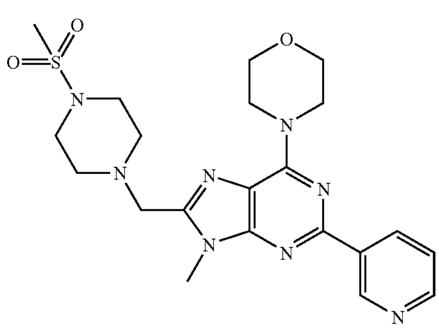 | 4-(9-methyl-8-((4-(methylsulfonyl)piperazin-1-yl)methyl)-2-(pyridin-3-yl)-9H-purin-6-yl)morpholine |

TABLE 1-continued

| No. | Structure | Name |
|---|---|---|
| 138 | 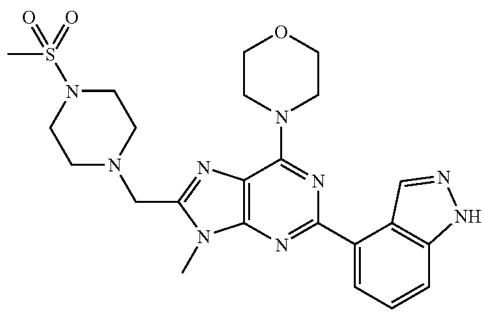 | 4-(2-(1H-indazol-4-yl)-9-methyl-8-((4-(methylsulfonyl)piperazin-1-yl)methyl)-9H-purin-6-yl)morpholine |
| 139 | 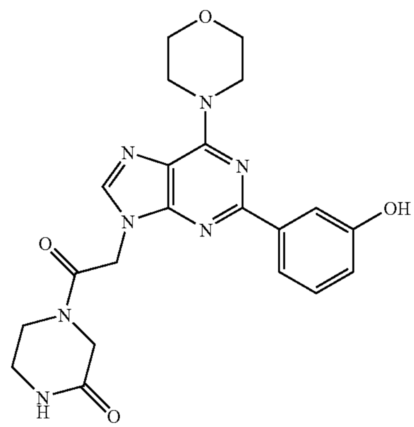 | 4-(2-(2-(3-hydroxyphenyl)-6-morpholino-9H-purin-9-yl)acetyl)piperazin-2-one |
| 140 | 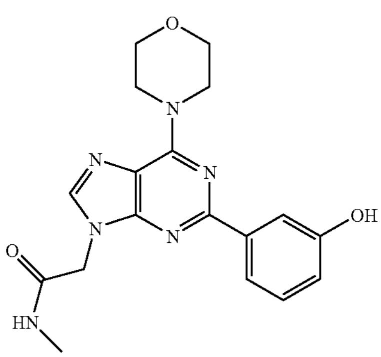 | 2-(2-(3-hydroxyphenyl)-6-morpholino-9H-purin-9-yl)-N-methylacetamide |
| 141 | 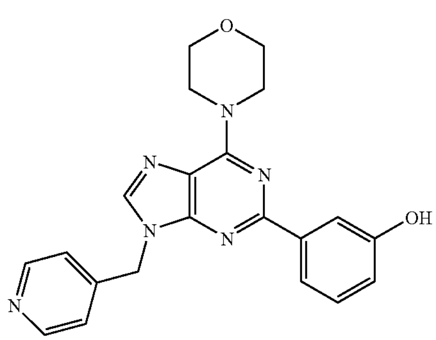 | 3-(6-morpholino-9-(pyridin-4-ylmethyl)-9H-purin-2-yl)pheno |

TABLE 1-continued

| No. | Structure | Name |
| --- | --- | --- |
| 142 | 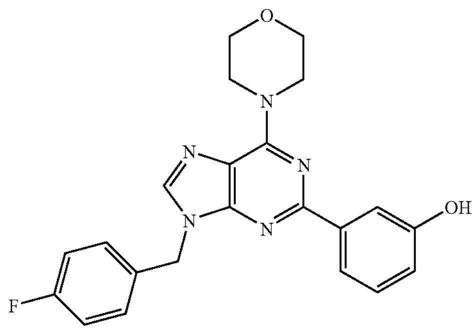 | 3-(9-(4-fluorobenzyl)-6-morpholino-9H-purin-2-yl)phenol |
| 143 | 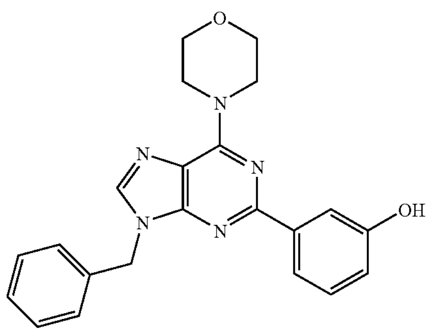 | 3-(9-benzyl-6-morpholino-9H-purin-2-yl)pheol |
| 144 | 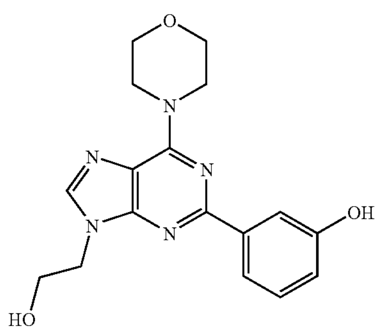 | 3-(9-(2-hydroxyethyl)-6-morpholino-9H-purin-2-yl)phenol |
| 145 | 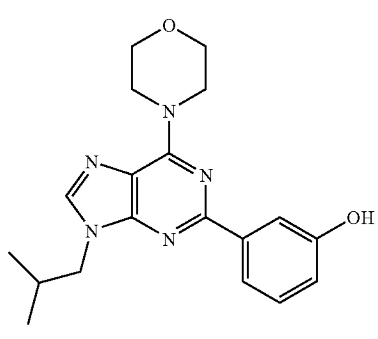 | 3-(9-isobutyl-6-morpholino-9H-purin-2-yl)phenol |

TABLE 1-continued

| No. | Structure | Name |
|---|---|---|
| 146 | 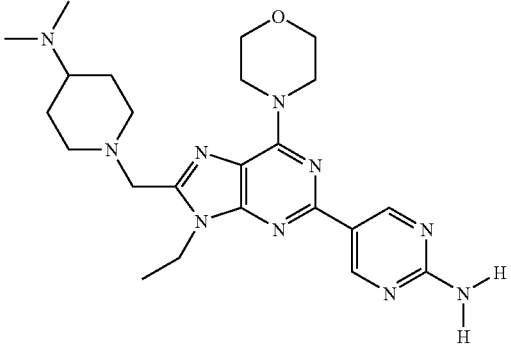 | 5-(8-((4-(dimethylamino)piperidin-1-yl)methyl)-9-ethyl-6-morpholino-9H-purin-2-yl)pyrimidin-2-amine |
| 147 | 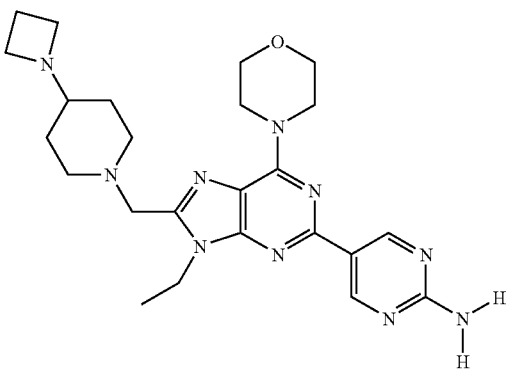 | 5-(8-((4-(azetidin-1-yl)piperidin-1-yl)methyl)-9-ethyl-6-morpholino-9H-purin-2-yl)pyrimidin-2-amine |
| 148 | 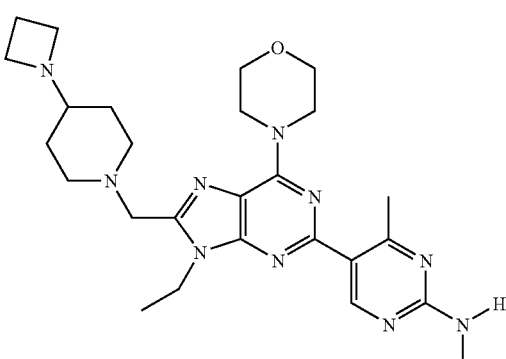 | 5-(8-((4-(azetidin-1-yl)piperidin-1-yl)methyl)-9-ethyl-6-morpholino-9H-purin-2-yl)-4-methylpyrimidi-2-amine |
| 149 | 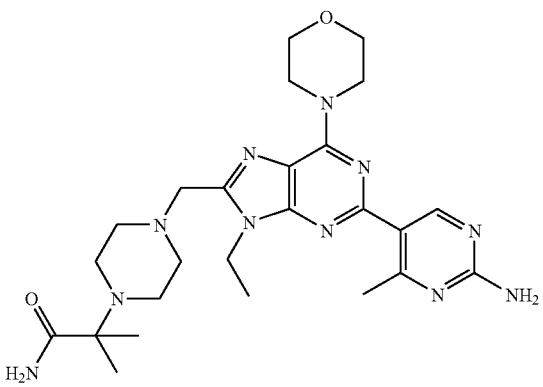 | 2-(4-((2-(2-amino-4-methylpyrimidin-5-yl)-9-ethyl-6-morpholino-9H-purin-8-yl)methyl)piperazin-1-yl)-2-methylpropanamide |

TABLE 1-continued

| No. | Structure | Name |
|---|---|---|
| 150 | 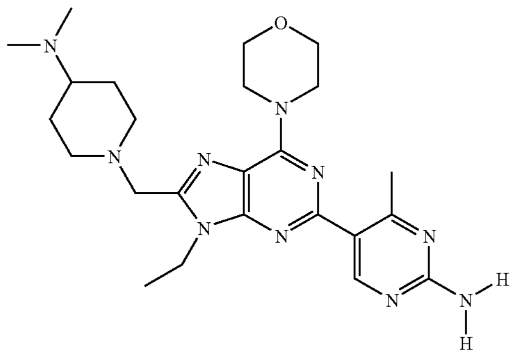 | 5-(8-((4-(dimethylamino)piperidin-1-yl)methyl)-9-ethyl-6-morpholino-9H-purin-2-yl)-4-methylpyrimidin-2-amine |
| 151 | 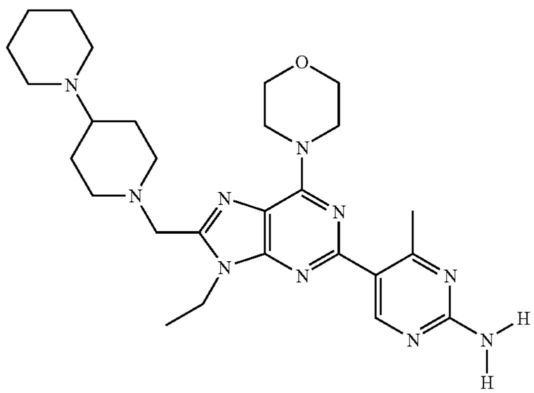 | 5-(8-(1,4'-bipiperidin-1'-ylmethyl)-9-ethyl-6-morpholino-9H-purin-2-yl)-4-methylpyrimidin-2-amine |
| 152 | 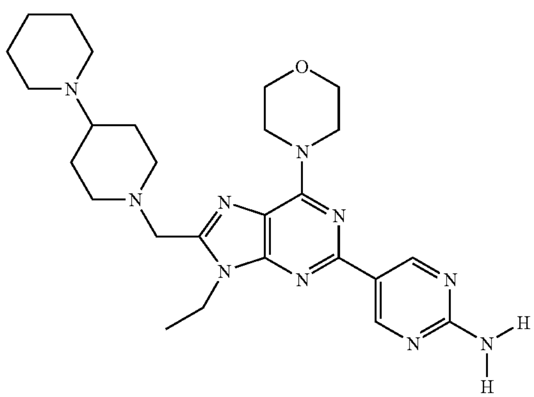 | 5-(8-(1,4'-bipiperidin-1'-ylmethyl)-9-ethyl-6-morpholino-9H-purin-2-yl)pyrimidin-2-amine |
| 153 | 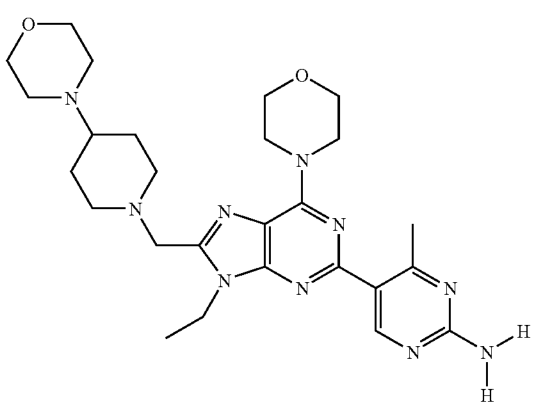 | 5-(9-ethyl-6-morpholino-8-((4-morpholinopiperidin-1-yl)methyl)-9H-purin-2-yl)-4-methylpyrimidin-2-amine |

TABLE 1-continued

| No. | Structure | Name |
|---|---|---|
| 154 | 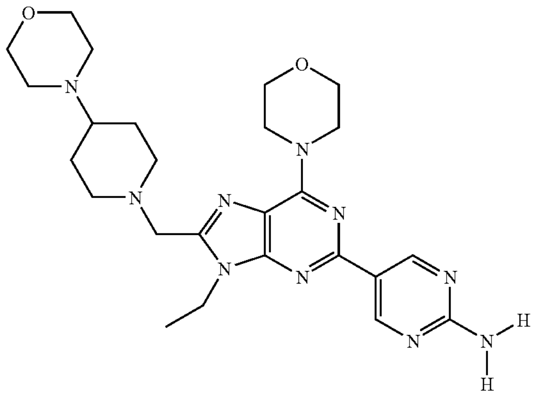 | 5-(9-ethyl-6-morpholino-8-((4-morpholinopiperidin-1-yl)methyl)-9H-purin-2-yl)pyrimidin-2-amine |
| 155 | 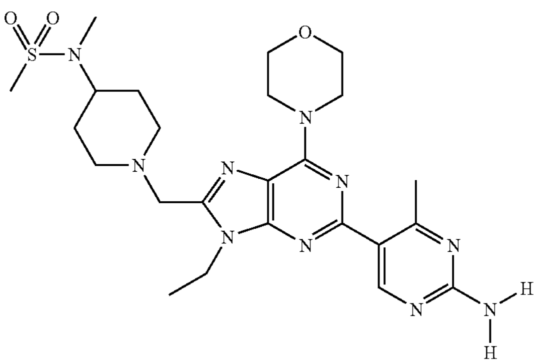 | N-(1-((2-(2-amino-4-methylpyrimidin-5-yl)-9-ethyl-6-morpholino-9H-purin-8-yl)methyl)piperidin-4-yl)-N-methylmethanesulfonamide |
| 156 | 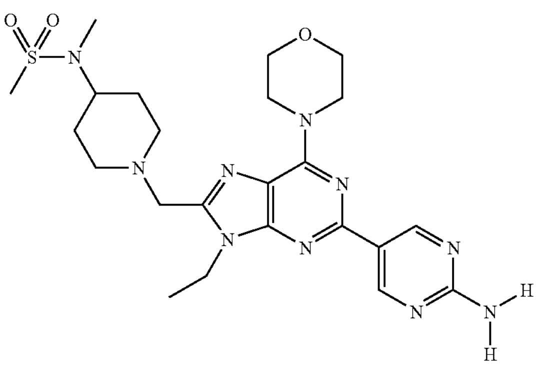 | N-(1-((2-(2-aminopyrimidin-5-yl)-9-ethyl-6-morpholino-9H-purin-8-yl)methyl)piperidin-4-yl)-N-methylmethanesulfonamide |

Administration of Compounds of Formula I

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Compounds of the present invention are useful for treating hyperproliferative diseases, conditions and/or disorders including, but not limited to, those characterized by over expression of lipid kinases, e.g. PI3 kinase. Accordingly, another aspect of this invention includes methods of treating or preventing diseases or conditions that can be treated or prevented by inhibiting lipid kinases, including PI3. In one embodiment, the method comprises administering to a mammal in need thereof a therapeutically effective amount of a compound of Formula I, or a stereoisomer, geometric isomer, tautomer, or pharmaceutically acceptable salt thereof. In one embodiment, a human patient is treated with a compound of Formula I and a pharmaceutically acceptable carrier, adjuvant, or vehicle, wherein said compound of Formula I is present in an amount to detectably inhibit PI3 kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Another aspect of this invention provides a compound of this invention for use in the treatment of the diseases or conditions described herein in a mammal, for example, a human, suffering from such disease or condition. Also provided is the use of a compound of this invention in the preparation of a medicament for the treatment of the diseases and conditions described herein in a warm-blooded animal, such as a mammal, for example a human, suffering from such disorder.

Pharmaceutical Formulations

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(-)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as a hyperproliferative disorder (e.g., cancer). In certain embodiments, a compound of Formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, geometric isomer, tautomer, solvate, metabolite, or pharmaceutically acceptable salt or prodrug thereof, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of Formula I, or a stereoisomer, geometric isomer, tautomer, solvate, metabolite, or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one compound of Formula I, or a stereoisomer, geometric isomer, tautomer, solvate, metabolite, or pharmaceutically acceptable salt or prodrug thereof, and the use of at least one other cancer treatment method. The amounts of the compound(s) of Formula I and the other pharmaceutically active chemotherapeutic agent(s) and the relative timings of administration will be selected in order to achieve the desired combined therapeutic effect.

Metabolites of Compounds of Formula I

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I, or a stereoisomer, geometric isomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

General Preparative Procedures

General Procedure A Suzuki Coupling:

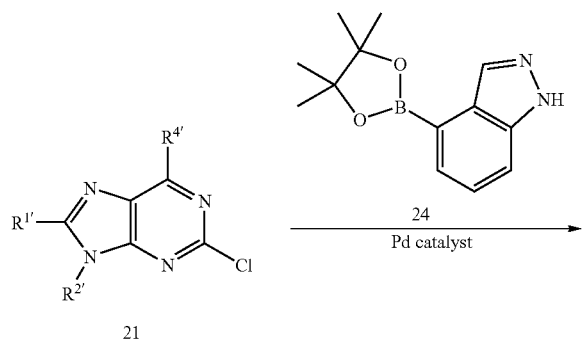

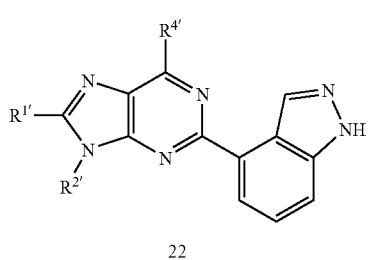

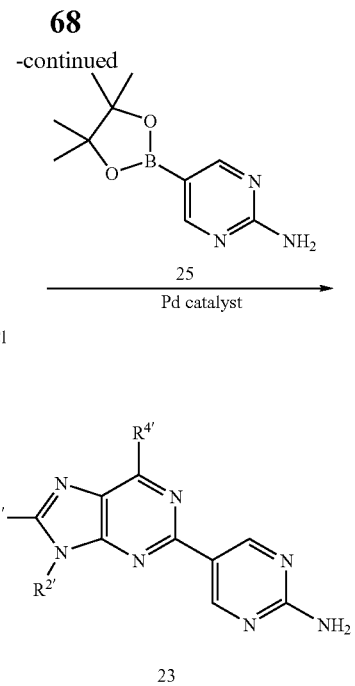

The Suzuki-type coupling reaction is useful to attach a monocyclic heteroaryl, a fused bicyclic heterocycle, a fused bicyclic heteroaryl, or a phenyl at the 2-position of the pyrimidine ring of a 2-chloro-purine 21. For example, 21 may be combined with 1.5 equivalents of 4-(4,4,5,5-tetramethyl-1,3,2-dioxaborolan-2-yl)1H-indazole 24, and dissolved in 3 equivalents of sodium carbonate as a 1 molar solution in water and an equal volume of acetonitrile. A catalytic amount, or more, of a low valent palladium reagent, such as bis(triphenylphosphine)palladium(II) dichloride, is added. A variety of boronic acids or boronic esters can be used in place of the indazole boronic ester indicated. Also alternatively, the nitrogen of the indazole may be protected, for example, N-THP protected compound 41. In some cases potassium acetate was used in place of sodium carbonate to adjust the pH of the aqueous layer. The reaction is then heated to about 140-150° C. under pressure in a microwave reactor such as the Biotage Optimizer (Biotage, Inc.) for 10 to 30 minutes. The contents are extracted with ethyl acetate, or another organic solvent. After evaporation of the organic layer the Suzuki coupling products, 6,8,9-substituted 2-(1H-indazol-4-yl)-purine 22, or 6,8,9-substituted 2-(5-pyrimidin-2-amine)-purine 23, may be purified on silica or by reverse phase HPLC. Substituents $R^{1'}$, $R^{2'}$, $R^{4'}$ may be $R^1$, $R^2$, $R^4$ as defined, or protected forms or precursors thereof.

A variety of palladium catalysts can be used during the Suzuki coupling step to form compounds, including exemplary embodiments 22 and 23. Suzuki coupling is a palladium mediated cross coupling reaction of an arylhalide, such as 21, with a boronic acid such as 24 or 25. Low valent, Pd(II) and Pd(0) catalysts may be used in the Suzuki coupling reaction, including $PdCl2(PPh_3)_2$, $Pd(t-Bu)_3$, $PdCl_2$ dppf $CH_2Cl_2$, $Pd(PPh_3)_4$, $Pd(OAc)/PPh_3$, $Cl_2Pd[(Pet_3)]_2$, $Pd(DIPHOS)_2$, $Cl_2Pd(Bipy)$, $[PdCl(Ph_2PCH_2PPh_2)]_2$, $Cl_2Pd[P(o-tol)_3]_2$, $Pd_2(dba)_3/P(o-tol)_3$, $Pd_2(dba)/P(furyl)_3$, $Cl_2Pd[P(furyl)_3]_2$, $Cl_2Pd(PMePh_2)_2$, $Cl_2Pd[P(4-F-Ph)_3]_2$, $Cl_2Pd[P(C_6F_6)_3]_2$, $Cl_2Pd[P(2-COOH-Ph)(Ph)_2]_2$, $Cl_2Pd[P(4-COOH-Ph)(Ph)_2]_2$, and encapsulated catalysts Pd EnCat™ 30, Pd EnCat™ TPP30, and Pd(II) EnCat™ BINAP30 (US 2004/0254066).

General Procedure B C-6 Nitrogen Substitution

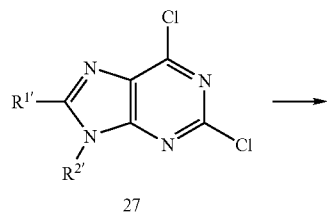

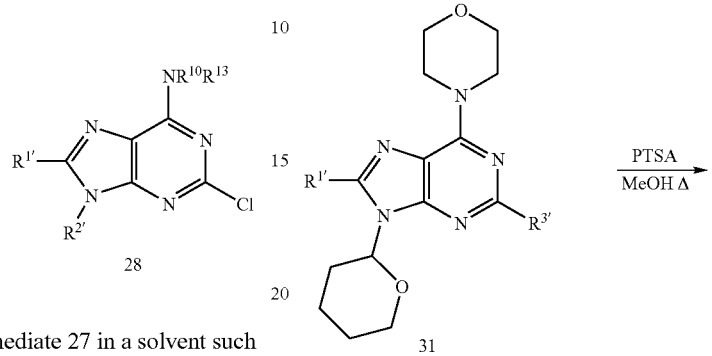

To a 2,6-dichloro purine intermediate 27 in a solvent such as ethanol is added a primary or secondary amine ($R^{10}R^{13}NH$, 1.1 equiv.) and a non-nucleophilic base such as triethylamine ($NEt_3$, 1.5 eq, 63 μl). Alternatively, acetonitrile may be used as the solvent and potassium carbonate may be used as the base. The reaction mixture is stirred at room temperature for about 1 hour or overnight, volatiles removed in vacuo and residue partitioned between DCM and brine. If the mixture is insoluble it may be sonicated and the solid product was collected by filtration. Drying with magnesium sulfate and evaporation of the solvent gives N'-(2-chloro purin-6-yl)-amine substituted intermediate 28, often as a crystalline solid, or by trituration. Substituents $R^{1'}$ and $R^{2'}$ may be $R^1$ and $R^2$ as defined, or protected forms or precursors thereof.

General Procedure C N-9 Nitrogen Alkylation

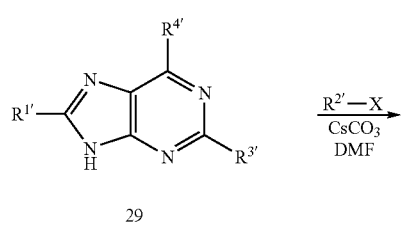

9-H Purine intermediate 29 is brought up into DMF and 2 equiv of cesium carbonate is added to the reaction mixture. The reaction is heated to 50° C. whereupon 3 equivalents of an alkyl halide $R^{2'}$—X are added to the reaction mixture. The reaction is monitored by TLC or LC/MS and stirred until completion, typically several hours. The reaction mixture is extracted with EtOAc and water, and the organic layer is dried, filtered and concentrated to get crude 9-alkylated purine 30 which is used directly in the next reaction or purified by reverse phase HPLC. Substituents $R^{1'}$, $R^{3'}$ and $R^{4'}$ may be $R^1$, $R^3$ and $R^4$ as defined, or protected forms or precursors thereof.

General Procedure D THP Deprotection

Generally, N-9-tetrahydropyranyl substituted 31 may be treated with catalytic amounts of para-toluenesulfonic acid (PTSA) in a solution of methanol and heated to about 50° C. until the tetrahydropyran (THP) group is removed to afford compound 32. The reaction may be monitored by LC-MS or TLC. Substituents $R^{1'}$ and $R^{3'}$ may be $R^1$ and $R^3$ as defined, or protected forms or precursors thereof.

General Procedure E Boc Deprotection

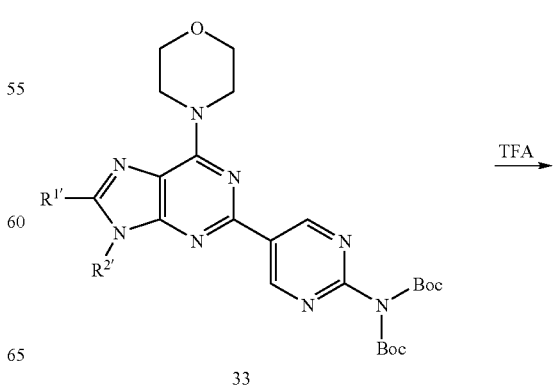

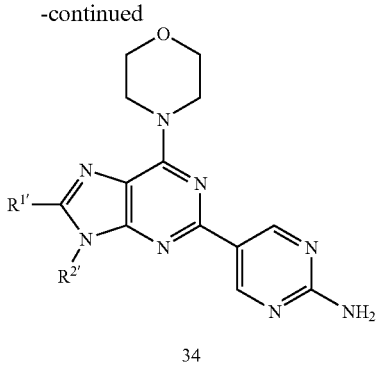

34

Generally, Boc-substituted 33 is treated with TFA or 4N HCl to remove the t-butoxycarbonyl group(s) and the reaction is monitored by LC-MS for completion. The crude product is then concentrated and purified by reverse phase HPLC to yield product 34 as a pure solid. Substituents $R^{1'}$ and $R^{2'}$ may be $R^1$ and $R^2$ as defined, or protected forms or precursors thereof.

General Procedure F Amide Coupling

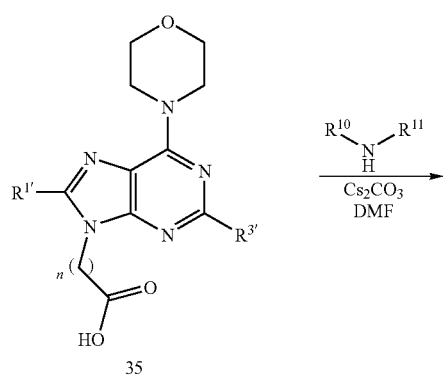

35

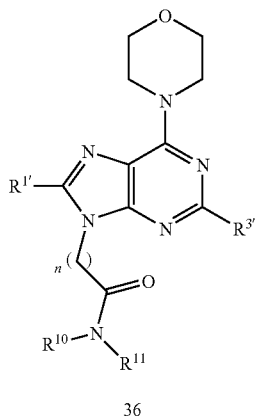

36

A 2,6,8 substituted, 9-alkylcarboxyl purine 35, where n is 1 to 12, is treated with 1.5 eq HATU (2-(7-aza-1H-benzotriazole-1-yl)-1,1,3,3-tetramethyluronium hexafluorophosphate), an excess (such as 3 eq) of an alkylamine ($HNR^{10}R^{11}$) and an excess (such as 3 eq) of cesium carbonate in dimethylformamide (DMF). Alternatively, other coupling reagents may be used. The reaction is stirred until complete and extracted in ethylacetate with saturated bicarbonate solution. The organic layer is dried, filtered and concentrated to yield the acylated, crude intermediate, which is purified via reverse phase HPLC to yield product 36. Substituents $R^{1'}$ and $R^{3'}$ may be $R^1$ and $R^3$ as defined, or protected forms or precursors thereof.

EXAMPLES

The chemical reactions described in the Examples may be readily adapted to prepare a number of other PI3K inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting reactive functional groups, by utilizing other suitable reagents known in the art other than those described, and/or by making routine modifications of reaction conditions. Alternatively, other reactions disclosed herein or known in the art will be recognized as having applicability for preparing other compounds of the invention.

In the Examples described below, unless otherwise indicated all temperatures are set forth in degrees Celsius. Reagents were purchased from commercial suppliers such as Sigma Aldrich Chemical Company, Lancaster, TCI or Maybridge, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted on a Biotage system (Manufacturer: Dyax Corporation) having a silica gel column or on a silica SEP PAK® cartridge (Waters). $^1$H NMR spectra were obtained at 400 MHz in deuterated CDCl$_3$, d$_6$-DMSO, CH$_3$OD or d$_6$-acetone solutions (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

2,6-dichloro-9-methyl-9H-purine 4

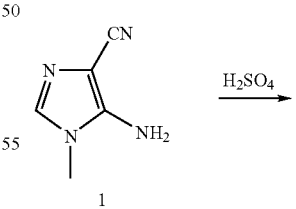

1

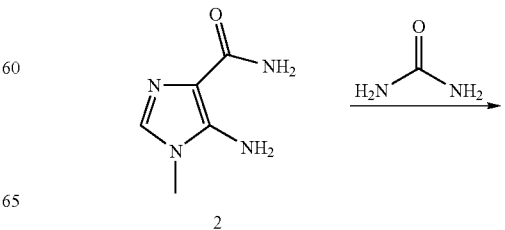

2

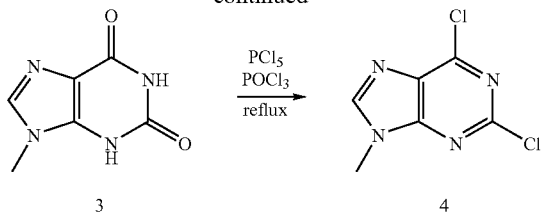

Example 2

4-(4,4,5,5-tetramethyl-[1,3,2]dioxaborolan-2-yl)-1H-indazole 24—route 1

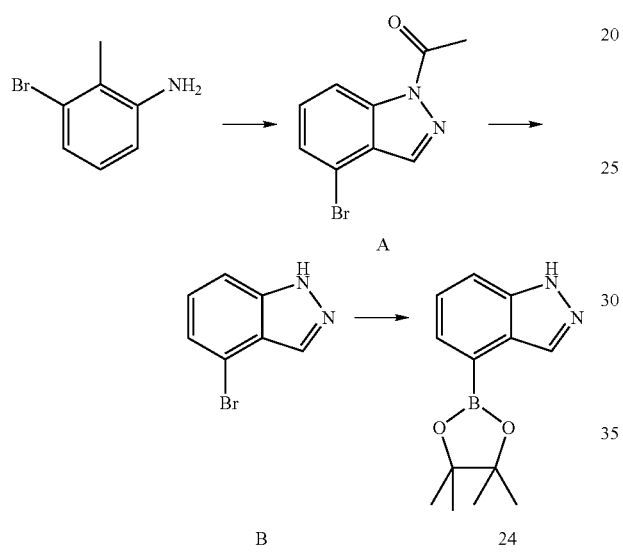

To a solution of 3-bromo-2-methyl aniline (5.0 g, 26.9 mmol) in chloroform (50 mL) was added potassium acetate (1.05 eq., 28.2 mmol, 2.77 g). Acetic anhydride (2.0 eq., 53.7 mmol, 5.07 mL) was added with concurrent cooling in ice-water. The mixture was then stirred at room temperature for 10 minutes after which time a white gelatinous solid formed. 18-Crown-6 (0.2 eq., 5.37 mmol, 1.42 g) was added followed by iso-amyl nitrite (2.2 eq., 59.1 mmol, 7.94 mL) and the mixture was heated under reflux for 18 h. The reaction mixture was allowed to cool, and was partitioned between chloroform (3×100 mL) and saturated aqueous sodium hydrogen carbonate (100 mL). The combined organic extracts were washed with brine (100 mL), separated and dried (MgSO$_4$).

The crude product was evaporated onto silica and purified by chromatography eluting with 20% to 40% EtOAc-petrol to give 1-(4-bromo-indazol-1-yl)-ethanone A (3.14 g, 49%) as an orange solid, and 4-bromo-1H-indazole B (2.13 g, 40%) as a pale orange solid. A $^1$H NMR (400 MHz, CDCl$_3$) 2.80 (3H, s), 7.41 (1H, t, J=7.8 Hz), 7.50 (1H, d, J=7.8 Hz), 8.15 (1H, s), 8.40 (1H, d, J=7.8 Hz). B: $^1$H NMR (400 MHz, CDCl$_3$) 7.25 (1H, t, J=7.3 Hz), 7.33 (1H, d, J=7.3 Hz), 7.46 (1H, d, J=7.3 Hz), 8.11 (1H, s), 10.20 (1H, br s).

To a solution of the 1-(4-bromo-indazol-1-yl)-ethanone A (3.09 g, 12.9 mmol) in MeOH (50 mL) was added 6N aqueous HCl (30 mL) and the mixture was stirred at room temperature for 7 h. The MeOH was evaporated and the mixture partitioned between EtOAc (2×50 mL) and water (50 mL). The combined organic layers were washed with brine (50 mL), separated and dried (MgSO$_4$). The solvent was removed by evaporation under reduced pressure to give 4-bromo-1H-indazole B (2.36 g, 93%).

To a solution of the 4-bromo-1H-indazole B (500 mg, 2.54 mmol) and bis(pinacolato)diboron (1.5 eq., 3.81 mmol) in DMSO (20 mL) was added potassium acetate (3.0 eq., 7.61 mmol, 747 mg; dried in drying pistol) and PdCl$_2$(dppf)$_2$ (3 mol %, 0.076 mmol, 62 mg). The mixture was degassed with argon and heated at 80° C. for 40 h. The reaction mixture was allowed to cool and partitioned between water (50 mL) and ether (3×50 mL). The combined organic layers were washed with brine (50 mL), separated and dried (MgSO$_4$). The crude material was purified by chromatography eluting with 30% to 40% EtOAc-petrol to give an inseparable 3:1 mixture of the 4-(4,4,5,5-tetramethyl-[1,3,2]dioxaborolan-2-yl)-1H-indazole 24 (369 mg, 60%) and indazole (60 mg, 20%), isolated as a yellow gum which solidified upon standing to furnish as an off-white solid. $^1$H NMR (400 MHz, d$_6$-DMSO) 1.41 (12H, s), 7.40 (1H, dd, J=8.4 Hz, 6.9 Hz), 7.59 (1H, d, J=8.4 Hz), 7.67 (1H, d, J=6.9 Hz), 10.00 (1H, br s), 8.45 (1H, s), and indazole: 7.40 (1H, t), 7.18 (1H, t, J=7.9 Hz), 7.50 (1H, d, J=9.1 Hz), 7.77 (1H, d, J=7.9 Hz), 8.09 (1H, s); impurity at 1.25.

Example 3

4-(4,4,5,5-Tetramethyl-[1,3,2]dioxaborolan-2-yl)-1H-indazole 24—route 2

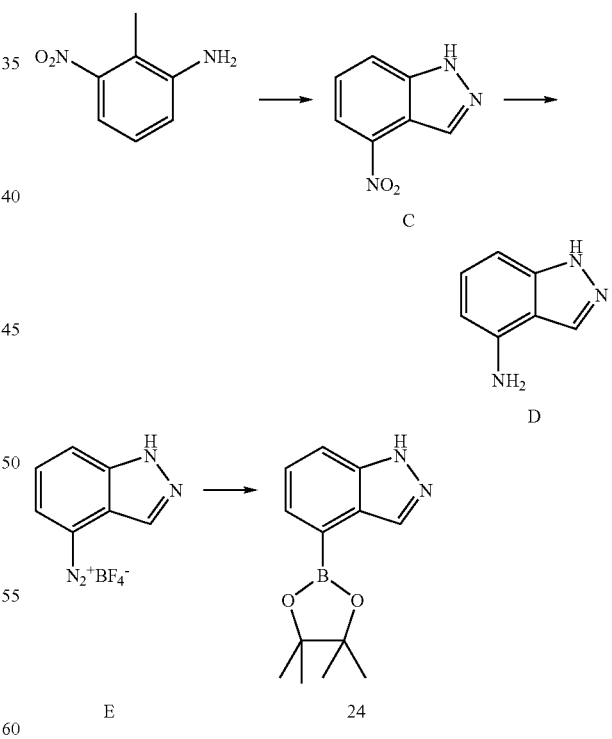

To a solution of 2-methyl-3-nitroaniline (2.27 g, 14.91 mmol) in acetic acid (60 mL) was added a solution of sodium nitrite (1.13 g, 1.1 eq.) in water (5 mL). After 2 h, the deep red solution was poured onto ice/water and the resulting precipitate collected by filtration to yield 4-nitro-1H-indazole C (1.98 g, 81%).

A mixture of 4-nitro-1H-indazole C (760 mg, 4.68 mmol), palladium on charcoal (10%, cat.) and ethanol (30 mL) was stirred under a balloon of hydrogen for 4 h. The reaction mixture was then filtered through celite, and the solvent removed in vacuo to yield 1H-indazol-4-ylamine D (631 mg, 100%).

An aqueous solution of sodium nitrite (337 mg, 4.89 mmol) in water (2 mL) was added dropwise to a suspension of 1H-indazol-4-ylamine D (631 mg, 4.74 mmol) in 6M hydrochloric acid (7.2 mL) at below 0° C. After stirring for 30 minutes, sodium tetrafluoroborate (724 mg) was added to the reaction mixture. A viscous solution resulted, which was filtered and washed briefly with water to yield 1H-indazole-4-diazonium tetrafluoroborate salt E (218 mg, 20%) as a deep red solid.

Dry methanol (4 mL) was purged with argon for 5 minutes. To this was added 1H-indazole-4-diazonium tetrafluoroborate salt (218 mg, 0.94 mmol), bis-pinacolato diboron (239 mg, 1.0 eq.) and [1,1'-bis(diphenylphosphino)ferrocene]palladium (II) chloride (20 mg). The reaction mixture was stirred for 5 h and then filtered through celite. The residue was purified using flash chromatography to yield 4-(4,4,5,5-tetramethyl-[1,3,2]dioxaborolan-2-yl)-1H-indazole 24 (117 mg).

Example 4

1-(Tetrahydro-2H-pyran-2-yl)-4-(4,4,5,5-tetramethyl-1,3,2-dioxaborolan-2-yl)-1H-indazole 41
(Route A)

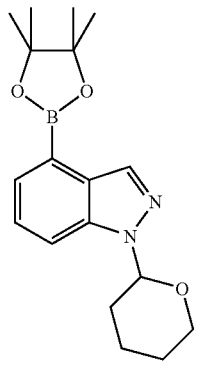

41

Step A: Preparation of 4-chloro-1H-indazole: To a 250 ml flask with stir bar was added 2-methyl-3-chloroaniline (8.4 ml, 9.95 g, 70.6 mmol), potassium acetate (8.3 g, 84.7 mmol) and chloroform (120 ml). This mixture was cooled to 0° C. with stirring. To the cooled mixture was added acetic anhydride (20.0 ml, 212 mmol) drop wise over 2 minutes. The reaction mixture was warmed to 25° C. and stirred for 1 hour. At this point, the reaction was heated to 60° C. Isoamyl nitrite (18.9 ml, 141 mmol) was added and the reaction was stirred overnight at 60° C. Once complete, water (75 ml) and THF (150 ml) were added and the reaction was cooled to 0° C. LiOH (20.7 g, 494 mmol) was added and the reaction was stirred at 0° C. for 3 hours. Water (200 ml) was added and the product was extracted with EtOAc (300 ml, 100 ml). The organic layers were combined, dried with $MgSO_4$ and concentrated in vacuo to yield 4-chloro-1H-indazole 11.07 g (100%) as an orange solid. $^1$H NMR (400 MHz, $CDCl_3$) δ 8.18 (d, J=1 Hz, 1H), 7.33 (d, J=8 Hz 1H), 7.31 (t, J=7 Hz, 1H), 7.17 (dd, J=7 Hz, 1 Hz 1H). LCMS (ESI pos) m/e 153 (M+1).

Step B: Preparation of 4-chloro-1-(tetrahydro-2H-pyran-2-yl)-1H-indazole: To a 1 L flask with mechanical stirrer was added 4-chloro-1H-indazole (75.0 g, 0.492 mol), pyridinium p-toluenesulfonate (1.24 g, 4.92 mmol), $CH_2Cl_2$ (500 ml) and 3,4-dihydro-2H-pyran (98.6 ml, 1.08 mol). With stirring, this mixture was heated to 45° C. for 16 hours. Analysis of reaction mixture shows production of both isomers of product. Cooled reaction to 25° C. and added $CH_2Cl_2$ (200 ml). Washed the solution with water (300 ml) and saturated $NaHCO_3$ (250 ml). Dried the organics with $MgSO_4$ and concentrated to dryness. Purified the crude product by dissolving in EtOAc/hexanes (4:6, 1 L) and adding $SiO_2$ (1.2 L). The mixture was filtered and the cake was washed with EtOAc/Hexanes (4:6, 2 L). The organics were concentrated in vacuo to yield 4-chloro-1-(tetrahydro-2H-pyran-2-yl)-1H-indazole 110.2 g (95%) as an orange solid. Isomer 1: $^1$H NMR (400 MHz, $CDCl_3$) δ 8.10 (d, J=1 Hz, 1H), 7.50 (dd, J=9 Hz, 1 Hz 1H), 7.29 (dd, J=9 Hz, 8 Hz 1H), 7.15 (dd, J=8 Hz, 1 Hz 1H) 5.71 (dd, J=9 Hz, 3 Hz 1H) 4.02 (m, 1H) 3.55 (m, 1H) 2.51 (m, 1H) 2.02 (m, 2H) 1.55 (m, 3H). LCMS (ESI pos) m/e 237 (M+1); Isomer 2: $^1$H NMR (400 MHz, $CDCl_3$) δ 8.25 (d, J=1 Hz, 1H), 7.62 (dd, J=9 Hz, 1 Hz 1H), 7.20 (dd, J=9 Hz, 8 Hz 1H), 7.06 (dd, J=8 Hz, 1 Hz 1H) 5.69 (dd, J=9 Hz, 3 Hz 1H) 4.15 (m, 1H) 3.80 (m, 1H) 2.22 (m, 2H) 2.05 (m, 1H) 1.75 (m, 3H). LCMS (ESI pos) m/e 237 (M+1).

Step C: Preparation of 1-(tetrahydro-2H-pyran-2-yl)-4-(4,4,5,5-tetramethyl-1,3,2-dioxaborolan-2-yl)-1H-indazole 41: To a 500 ml flask with stir bar was added 4-chloro-1-(tetrahydro-2H-pyran-2-yl)-1H-indazole (10.0 g, 42.2 mmol), DMSO (176 ml), $PdCl_2(PPh_3)_2$ (6.2 g, 8.86 mmol), tricyclohexylphosphine (0.47 g, 1.69 mmol), bis(pinacolato)diboron (16.1 g, 63.4 mmol) and potassium acetate (12.4 g, 0.127 mol). With stirring, the mixture was heated to 130° C. for 16 hours. The reaction was cooled to 25° C. and EtOAc (600 ml) was added and washed with water (2×250 ml). The organics were dried with $MgSO_4$ and concentrated in vacuo to dryness. The crude product was purified by $SiO_2$ plug (120 g), eluting with 10% EtOAc/Hexanes (1 L) and 30% EtOAc/Hexanes (1 L). The filtrate was concentrated in vacuo to give 13.9 g (100%) of product 41 as a 20% (wt/wt) solution in ethyl acetate. $^1$H NMR shows the presence of about 20% (wt/wt) bis(pinacolato)diboron. $^1$H NMR (400 MHz, $CDCl_3$) δ 8.37 (s, 1H), 7.62 (dd, J=14 Hz, 2 Hz 1H), 7.60 (dd, J=7 Hz, 1 Hz 1H), 7.31 (dd, J=8 Hz, 7 Hz 1H) 5.65 (dd, J=9 Hz, 3 Hz 1H) 4.05 (m, 1H) 3.75 (m, 1H) 2.59 (m, 1H) 2.15 (m, 1H) 2.05 (m, 1H) 1.75 (m, 3H) 1.34 (s, 12H). LCMS (ESI pos) m/e 245 (M+1).

Example 5

1-(Tetrahydro-2H-pyran-2-yl)-4-(4,4,5,5-tetramethyl-1,3,2 dioxaborolan-2-yl)-1H-indazole 41
(Route B)

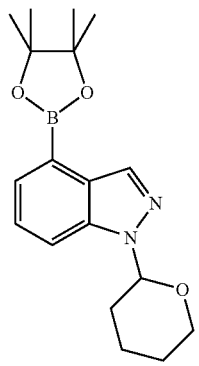

41

Step A: Preparation of 4-nitro-1H-indazole: A mixture of 2-methyl-3-nitro aniline (200 g, 1.315 moles), acetic acid (8000 ml) was cooled to 15-20° C. and a solution of sodium nitrite (90.6 g, 1.315 moles) in water (200 ml) was slowly added over 30 min. After the addition, the reaction temp. was increased to 25-30° C. and the reaction was stirred at this temp for 2-3 h. Reaction progress was monitored by TLC and after completion of reaction product was filtered and residue was washed with acetic acid (1000 ml). Acetic acid was distilled under vacuum (550 mm of Hg) below 80° C. and water (8000 ml) was added, cooled to 25-30° C. and stirred for 30 min. The slurry was filtered and washed with water (1000 ml). Crude product was dried under heating at 70-80° C. for 2 hours, then was taken in 5% ethyl acetate/n-hexane (100:2000 ml) solution and stirred for 1-1.5 h at ambient temperature. The suspension was filtered and washed with 5% ethyl acetate/n-hexane mixture (25:475 ml). The product obtained was dried under vacuum at below 80° C. for 10-12 h to give 4-nitro-1H-indazole as a brown solid (150 g, 70%): mp: 200-203° C.; $^1$H NMR (200 MHz, CDCl$_3$) δ 13.4 (br, 1H), 8.6 (s, 1H), 8.2-7.95 (dd, 2H), 7.4 (m, 1H). ESMS m/z 164 (M+1). Purity: 95% (HPLC)

Step B: Preparation of 4-amino-1H-indazole: A mixture of 4-nitro-1H-indazole (200 g, 1.22 moles) and 10% palladium on carbon (20.0 g,) in EtOH (3000 ml) was hydrogenated at ambient temperature (reaction was exothermic and temperature increased to 50° C.). After completion of reaction, the catalyst was removed by filtration. The solvent was evaporated under vacuum at below 80° C. and cooled to room temperature and n-hexane (1000 ml) was added to the residue and stirred for 30 min. Isolated solid was filtered and washed with n-hexane (200 ml). Product was dried under vacuum at 70-80° C. for 10-12 h to give 4-amino-1H-indazole as a brown solid (114 g, 70%), m.p.: 136-143° C. $^1$H NMR (200 MHz, CDCl$_3$) δ 12 (br, 1H), 8.0 (s, 1H), 7.1-7.0 (dd, 2H), 6.5 (d, 1H), 3.9 (m, 2H). ESMS m/z 134 (M+1). Purity: 90-95% (HPLC)

Step C: Preparation of 4-iodo-1H-indazole: A mixture of 4-amino-1H-indazole (50.0 g, 0.375 moles) in water (100 ml) and con. hydrochloric acid (182 ml) was cooled to −10° C. To this a solution of sodium nitrite (51.7 g, 0.75 moles) in water (75 ml) was added drop wise at −10° C. in about 30-60 min. (during addition frothing was observed). In another flask a mixture of potassium iodide (311 g, 1.87 moles) in water (3000 ml) was prepared at room temperature and to this above cooled diazonium salt at 30-40° C. was added in about 30-40 min. The reaction was maintained at 30° C. for 1 h and after completion of reaction, ethyl acetate (500 ml) was added and the reaction mixture was filtered through Celite. The layers were separated and the aq. layer was extracted with ethyl acetate (2×500 ml). The combined organic layers were washed with 5% hypo solution (2×500 ml), brine (500 ml), dried (Na$_2$SO$_4$) and concentrated. Crude product was purified by chromatography (silica gel, hexane, 15-20% ethyl acetate/hexane) to furnish 4-iodo-1H-indazole as an orange solid (23.0 g, 25%). mp: 151-177 C: $^1$H NMR (200 MHz, CDCl$_3$) δ 12.4 (br, 1H), 8.0 (s, 1H), 7.6 (dd, 2H), 7.1 (d, 1H). ESMS m/z 245 (M+1). Purity: 95-98% (HPLC).

Step D: Preparation of 4-iodo-1-(2-tetrahydropyranyl) indazole: A mixture of 4-amino-1H-indazole (250.0 g, 1.024 moles), 3,4-dihydro-2H-pyran (126.0 g, 1.5 moles) and PPTS (2.57 g, 0.01 moles) in CH$_2$Cl$_2$ (1250 ml) was heated to 50° C. for 2 h. The reaction was cooled to room temperature and poured into water (625 ml), the layers were separated, and aqueous layer was extracted with CH$_2$Cl$_2$ (250 ml). The combined organic layers were washed with water (625 ml), dried (Na$_2$SO$_4$) and concentrated. Crude residue was purified by chromatography (silica gel, hexane, 5-10% ethyl acetate/hexane) to furnish 4-iodo-1-(2-tetrahydropyranyl) indazole as an oil (807.0 g, 60%). $^1$H NMR (200 MHz, CDCl$_3$) δ 8.5 (s, 1H), 7.8 (m, 1H), 7.6 (d, 1H), 7.25 (m, 1H), 5.7 (dd, 1H), 4.2-3.8 (dd, 1H), 2.2-2.0 (m, 4H) 2.0-1.8 (m, 4H). ESMS m/z 329 (M+1).

Step E: Preparation of 1-(tetrahydro-2H-pyran-2-yl)-4-(4,4,5,5-tetramethyl-1,3,2-dioxaborolan-2-yl)-1H-indazole 41: A mixture of 4-iodo-1-(2-tetrahydropyranyl) indazole (100 g, 0.304 moles), bispinacalotodiborane (96.4 g, 0.381 moles), PdCl$_2$ (dppf) (8.91 g, 0.012 moles) and potassium acetate (85.97 g, 0.905 moles) in DMSO (500 ml) were heated to 80° C. for 2-3 h. After completion, reaction was cooled to room temperature and water (1500 ml) was added. Reaction mass was extracted into ethyl acetate (3×200 ml) and combined organic layers were evaporated, dried (Na$_2$SO$_4$) and concentrated. Crude product was purified by column chromatography (silica gel, hexane, 5-10% ethyl acetate/hexane) to obtain 41 as viscous brown oil (70.0 g, 70%). $^1$H NMR (CDCl$_3$) δ 8.5 (s, 1H), 7.8 (m, 1H), 7.6 (d, 1H), 7.25 (m, 1H), 5.7 (dd, 1H), 4.2-3.8 (dd, 1H), 2.2-2.0 (m, 4H) 2.0-1.8 (m, 4H) 1.4-1.2 (s, 12H). ESMS m/z 329 (M+1)

Example 6

4-methyl-5-(4,4,5,5-tetramethyl (1,3,2-dioxaborolan-2-yl)) pyrimidine-2-ylamine 42

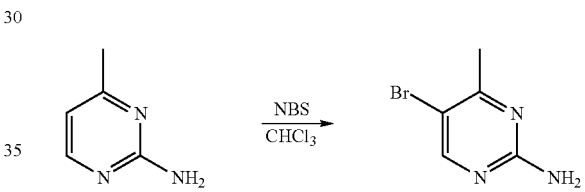

To a solution of 4-methylpyrimidine-2-ylamine (8.0 g, 0.073 mol) in chloroform (320 mL) was added N-bromosuccinimide (13.7 g, 0.077 mol). The reaction mixture was stirred in the dark for 18 hrs. LC/MS indicated the reaction was completed. The mixture was diluted with DCM, then washed with 1N NaOH aq solution and brine, dried over MgSO$_4$, filtered and concentrated to yield 5-bromo-4-methylpyrimidine-2-ylamin (12 g, Yield: 86%).

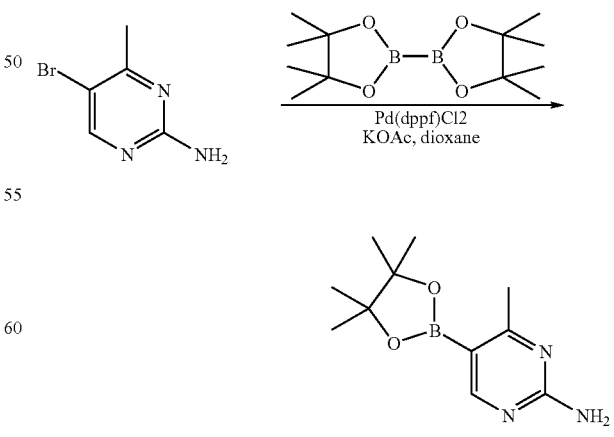

42

A mixture of 5-bromo-4-methylpyrimidine-2-ylamine (5.0 g, 26 mmol), potassium acetate (7.83 g, 79.8 mmol), 4,4,5,5-tetramethyl-2-(4,4,5,5-tetramethyl-1,3,2-dioxaborolan-2-yl)-1,3,2-dioxaborolane (7.43 g, 29.2 mmol) in dioxane (140 mL) was stirred for 20 min under nitrogen. 1,1'-bis(diphenylphosphino) ferrocene palladium (II) chloride dichloromethane adduct (1.08 g, 1.33 mmol) was added to the reaction mixture. The reaction mixture was heated to 115° C. for 18 h under nitrogen. Upon completion, the mixture was cooled and EtOAc was added. The resulting mixture was sonicated and filtered. Additional EtOAc was used to wash the solid. The combined organic extracts were washed with water, dried over $MgSO_4$, filtered and concentrated. The crude was purified by chromatography eluting with 20~100% EtOAc/hexane to yield 4.5 g of 42 (yield: 74%). $^1$H-NMR (DMSO, 400 MHz): δ 8.28 (s, 1H), 6.86 (br s, 2H), 2.35 (s, 3H), 1.25 (s, 12H). MS (ESI) m/e (M+H$^+$) 236.15, 154.07.

Example 7

2-(9-(2-hydroxyethyl)-2-(1H-indol-4-yl)-6-morpholino-9H-purin-8-yl)propan-2l 101

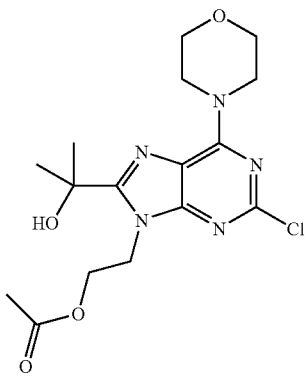

2-(2-Chloro-8-(2-hydroxypropan-2-yl)-6-morpholino-9H-purin-9-yl)ethyl acetate (165 mg) was treated with indole-4-boronic acid via General Procedure A and purified via reverse phase HPLC to give 21 mg of 101 as a white solid. MS (Q1) 423.2 (M)+

Example 8

2-(2-(2-amino-4-methylpyrimidin-5-yl)-9-(2-hydroxyethyl)-6-morpholino-9H-purin-8-yl)propan-2-ol 102

2-(2-Chloro-8-(2-hydroxypropan-2-yl)-6-morpholino-9H-purin-9-yl)ethyl acetate (300 mg) was treated with 4-methyl-5-(4,4,5,5-tetramethyl-1,3,2-dioxaborolan-2-yl)pyrimidin-2-amine via General Procedure A and was purified via reverse phase HPLC to give 107 mg of 102 as a white solid. MS (Q1) 415.2 (M)+

Example 9

2-(2-(2-aminopyrimidin-5-yl)-9-butyl-6-morpholino-9H-purin-8-yl)propan-2-ol 103

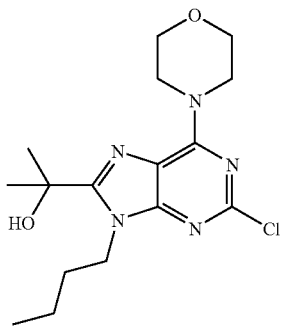

2-(2-Chloro-6-morpholino-9H-purin-8-yl)propan-2-ol 100 mg was treated with bromobutane via General Procedure C to give crude intermediate 2-(9-butyl-2-chloro-6-morpholino-9H-purin-8-yl)propan-2-ol which was treated with 2-aminopyrimidine-5-boronic acid, pinacol ester via General Procedure A and was purified via reverse phase HPLC to give 55 mg of 103 as a white solid. MS (Q1) 413.3 (M)+.

Example 10

2-(2-(2-aminopyrimidin-5-yl)-6-morpholino-9-propyl-9H-purin-8-yl)propan-2-ol 104

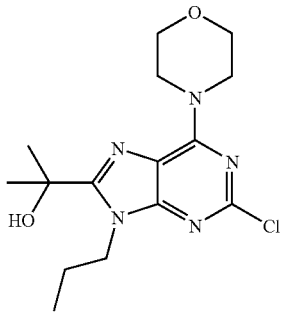

2-(2-Chloro-6-morpholino-9H-purin-8-yl)propan-2-ol (100 mg) was treated with iodopropane via General Procedure C to give crude intermediate 2-(2-chloro-6-morpholino-9-propyl-9H-purin-8-yl)propan-2-ol which was treated with 2-aminopyrimidine-5-boronic acid, pinacol ester via General Procedure A and was purified via reverse phase HPLC to give 34 mg of 104 as a white solid. MS (Q1) 399.3 (M)+.

Example 11

3-(2-(2-aminopyrimidin-5-yl)-8-(2-hydroxypropan-2-yl)-6-morpholino-9H-purin-9-yl)propan-1-ol 105

100 mg of 2-(2-chloro-6-morpholino-9H-purin-8-yl)propan-2-ol was treated with TBDMS-protected bromopropanol via General Procedure C. Crude intermediate 2-(9-(3-(tert-butyldimethylsilyloxy)propyl)-2-chloro-6-morpholino-9H-purin-8-yl)propan-2-ol was treated with 2-aminopyrimidine-5-boronic acid, pinacol ester via General Procedure A and was purified via reverse phase HPLC to give 36 mg of 105 as a white solid. MS (Q1) 415.2 (M)+.

Example 12

3-(2-(2-aminopyrimidin-5-yl)-8-(2-hydroxypropan-2-yl)-6-morpholino-9H-purin-9-yl)propan-1-ol 106

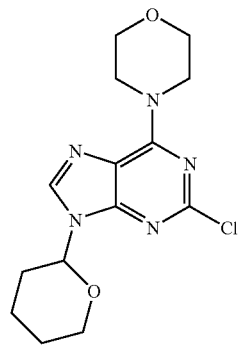

2,6-Dichloropurine (3 gm) was brought up into 20 mL EtOAc, and 100 mg PTSA was added. Dihydropyran (3 mL) was slowly added to the heterogeneous mixture while being heated until the reaction mixture was homogeneous. The reaction mixture was then extracted with a saturated bicarbonate solution three times. The organic layer was dried, filtered and concentrated to dryness. Crude 2,6-dichloro-9-(tetrahydro-2H-pyran-2-yl)-9H-purine was brought up in MeOH upon which morpholine (3 eq) was added. 4-(2-Chloro-9-(tetrahydro-2H-pyran-2-yl)-9H-purin-6-yl)morpholine slowly precipitated out of solution over the next 3 hours, then filtered, collected and dried to afford 4.26 g as a white solid.

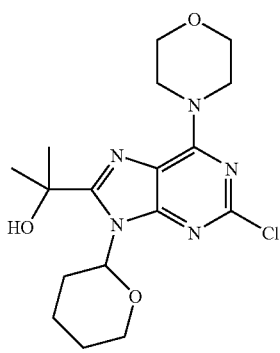

4-(2-Chloro-9-(tetrahydro-2H-pyran-2-yl)-9H-purin-6-yl)morpholine (2.76 gm) was cooled in THF to −78° C. A 2.5 M solution of n-BuLi in THF (1.5 eq) was added dropwise over 20 minutes. The reaction was stirred at −78° C. for 30 mins, after which acetone (1.56 mL) was added and the reaction was stirred over 2 hours, slowly warming to 0° C. The reaction mixture was then quenched with water and extracted with ethyl acetate. The crude product 2-(2-chloro-6-morpholino-9-(tetrahydro-2H-pyran-2-yl)-9H-purin-8-yl)propan-2-ol was concentrated and brought up in MeOH. The THP group was then removed via General Procedure D. The reaction mixture was concentrated and the crude solid was brought up in water, filtered and collected and dried overnight to give 2.23 gm of 2-(2-chloro-6-morpholino-9H-purin-8-yl)propan-2-ol as a light yellow solid.

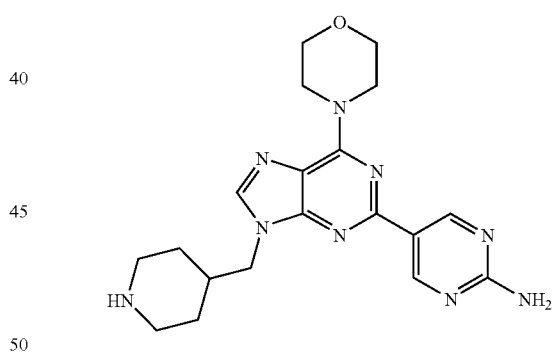

100 mg of 2-(2-chloro-6-morpholino-9H-purin-8-yl)propan-2-ol was treated with 2-bromoethyl acetate via General Procedure C. Crude intermediate 2-(2-chloro-8-(2-hydroxypropan-2-yl)-6-morpholino-9H-purin-9-yl)ethyl acetate was treated with 2-aminopyrimidine-5-boronic acid, pinacol ester via General Procedure A and was purified via reverse phase HPLC to give 54 mg of 106 as a white solid. MS (Q1) 401.2 (M)+.

Example 13

1-(4-((2-(2-aminopyrimidin-5-yl)-6-morpholino-9H-purin-9-yl)methyl)piperidin-1-yl)ethanone 107

2-(2-(2-(Bis(tert-butoxycarbonyl)amino)pyrimidin-5-yl)-6-morpholino-9H-purin-2-yl (400 mg) was reacted with tert-butyl 4-(bromomethyl)piperidine-1-carboxylate via General Procedure C to give tert-butyl 4-((2-(2-(bis(tert-butoxycarbonyl)amino)pyrimidin-5-yl)-6-morpholino-9H-purin-9-yl)methyl)piperidine-1-carboxylate (554 mg) which was subjected to Boc deprotection via General Procedure D to give 5-(6-morpholino-9-(piperidin-4-ylmethyl)-9H-purin-2-yl)pyrimidin-2-amine (454 mg) as yellow solid.

5-(6-Morpholino-9-(piperidin-4-ylmethyl)-9H-purin-2-yl)pyrimidin-2-amine (75 mg) was reacted with excess acetic acid, 2 eq HOBT, 5 eq diisopropylethylamine and 2 eq N-(3-dimethylaminopropyl)-N'-ethylcarbodiimide hydrochloride in 1 mL of DMF. Upon completion, the reaction was extracted with ethyl acetate and a saturated sodium bicarbonate solution. The organic layer was concentrated and purified via reverse phase HPLC to give 18.9 mg 107 as a white solid. MS (Q1) 438.3 (M)+

Example 14

1-(3-((2-(2-aminopyrimidin-5-yl)-6-morpholino-9H-purin-9-yl)methyl)pyrrolidin-1-yl)ethanone 108

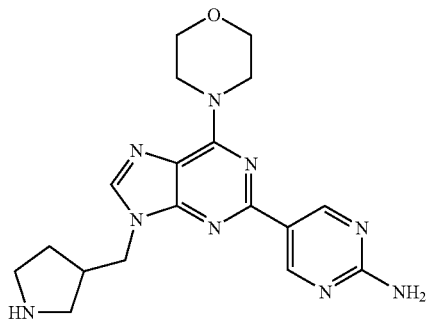

2-(2-(2-(Bis(tert-butoxycarbonyl)amino)pyrimidin-5-yl)-6-morpholino-9H-purin-2-yl (400 mg) was reacted with tert-butyl 3-(bromomethyl)pyrrolidine-1-carboxylate via General Procedure C to give tert-butyl 3-((2-(2-(bis(tert-butoxycarbonyl)amino)pyrimidin-5-yl)-6-morpholino-9H-purin-9-yl)methyl)pyrrolidine-1-carboxylate (496 mg) which was subjected to Boc deprotection via General Procedure D to yield 352 mg 5-(6-morpholino-9-(pyrrolidin-3-ylmethyl)-9H-purin-2-yl)pyrimidin-2-amine as yellow solid.

5-(6-Morpholino-9-(pyrrolidin-3-ylmethyl)-9H-purin-2-yl)pyrimidin-2-amine (75 mg) was reacted with excess acetic acid, 2 eq HOBT, 5 eq diisopropylethylamine and 2 eq N-(3-dimethylaminopropyl)-N'-ethylcarbodiimide Hydrochloride in 1 mL of DMF. Upon completion, the reaction was extracted with ethyl acetate and a saturated sodium bicarbonate solution. The organic layer was concentrated and purified via reverse phase HPLC to give 40.1 mg 108 as a white solid. MS (Q1) 424.2 (M)+.

Example 15

(R)-3-(2-(2-aminopyrimidin-5-yl)-6-morpholino-9H-purin-9-yl)-1-(3-hydroxypyrrolidin-1-yl)propan-1-one 109

3-(2-(2-(Tert-butoxycarbonylamino)pyrimidin-5-yl)-6-morpholino-9H-purin-9-yl)propanoic acid (50 mg) was reacted with (R)-pyrrolidin-3-ol via General Procedure F followed by Boc deprotection via General Procedure E to give 10.9 mg 109 as white solid following reverse phase purification. MS (Q1) 440.2 (M)+

Example 16

(S)-3-(2-(2-aminopyrimidin-5-yl)-6-morpholino-9H-purin-9-yl)-1-(3-hydroxypyrrolidin-1-yl)propan-1-one 110

3-(2-(2-(Tert-butoxycarbonylamino)pyrimidin-5-yl)-6-morpholino-9H-purin-9-yl)propanoic acid (50 mg) was reacted with (S)-pyrrolidin-3-ol via General Procedure F followed by Boc deprotection via General Procedure E to give 10.1 mg 110 as white solid following reverse phase purification. MS (Q1) 440.2 (M)+

Example 17

1-(3-(2-(2-aminopyrimidin-5-yl)-6-morpholino-9H-purin-9-yl)propanoyl)-N-methylpiperidine-4-carboxamide 111

3-(2-(2-(Tert-butoxycarbonylamino)pyrimidin-5-yl)-6-morpholino-9H-purin-9-yl)propanoic acid (50 mg) was reacted with N-methylpiperidine-4-carboxamide via General Procedure F followed by Boc deprotection via General Procedure E to give 10.9 mg 111 as white solid following reverse phase purification. MS (Q1) 495.3 (M)+

Example 18

3-(2-(2-aminopyrimidin-5-yl)-6-morpholino-9H-purin-9-yl)-1-(4-(methylsulfonyl)piperazin-1-yl)propan-1-one 112

3-(2-(2-(Tert-butoxycarbonylamino)pyrimidin-5-yl)-6-morpholino-9H-purin-9-yl)propanoic acid (50 mg) was reacted with 1-(methylsulfonyl)piperazine via General Procedure F followed by Boc deprotection via General Procedure E to give 33.8 mg 112 as white solid following reverse phase purification. MS (Q1) 517.2 (M)+

Example 19

3-(2-(2-aminopyrimidin-5-yl)-6-morpholino-9H-purin-9-yl) 1-morpholinopropan-1-one 113

3-(2-(2-(Tert-butoxycarbonylamino)pyrimidin-5-yl)-6-morpholino-9H-purin-9-yl)propanoic acid (50 mg) was reacted with morpholine via General Procedure F followed by Boc deprotection via General Procedure E to give 24.9 mg 113 as white solid following reverse phase purification. MS (Q1) 440.2 (M)+

Example 20

3-(2-(2-aminopyrimidin-5-yl)-6-morpholino-9H-purin-9-yl)propanoic acid 114

2-(2-(2-(Bis(tert-butoxycarbonyl)amino)pyrimidin-5-yl)-6-morpholino-9H-purin-2-yl (400 mg) was reacted with methyl 3-bromopropionate via General Procedure C. The product, 468 mg of crude methyl 3-(2-(2-(bis(tert-butoxycarbonyl)amino)pyrimidin-5-yl)-6-morpholino-9H-purin-9-yl)propanoate, was reacted with 3 eq of lithium hydroxide in 1:1 THF/Water solution. After completion, the THF was removed under vacuum and the water solution was acidified to pH 2 using a concentrated HCl solution. The product precipitated as a white solid and was filtered to yield 388 mg 3-(2-(2-(tert butoxycarbonylamino)pyrimidin-5-yl)-6-morpholino-9H-purin-9-yl)propanoic acid of which 88 mg was subjected to Boc deprotection via General Procedure E to give 15.5 mg 114 as white solid following reverse phase purification. MS (Q1) 371.2 (M)+

Example 21

5-(9-(4-(methylsulfonyl)benzyl)-6-morpholino-9H-purin-2-yl)pyrimidin-2-amine 115

2-(2-(2-(Bis(tert-butoxycarbonyl)amino)pyrimidin-5-yl)-6-morpholino-9H-purin-2-yl (100 mg) was reacted with 1-(chloromethyl)-4-(methylsulfonyl)benzene via General Procedure C followed by Boc deprotection via General Procedure E to give 25.4 mg 115 as white solid following reverse phase purification. MS (Q1) 467.2 (M)+

Example 22 methyl 4-((2-(2-aminopyrimidin-5-yl)-6-morpholino-9H-purin-9-yl)methyl)benzoate 116

2-(2-(2-(Bis(tert-butoxycarbonyl)amino)pyrimidin-5-yl)-6-morpholino-9H-purin-2-yl (100 mg) was reacted with methyl 4-(bromomethyl)benzoate via General Procedure C followed by Boc deprotection via General Procedure E to give 10.2 mg 116 as white solid following reverse phase purification. MS (Q1) 447.2 (M)+

Example 23

5-(6-morpholino-9-(2-morpholinoethyl)-9H-purin-2-yl)pyrimidin-2-amine 117

2-(2-(2-(Bis(tert-butoxycarbonyl)amino)pyrimidin-5-yl)-6-morpholino-9H-purin-2-yl (100 mg) was reacted with 4-(2-bromoethyl)morpholine via General Procedure C followed by Boc deprotection via General Procedure E to give 15.9 mg 117 as white solid following reverse phase purification. MS (Q1) 412.2 (M)+

Example 24

5-(9-(3-methoxybenzyl)-6-morpholino-9H-purin-2-yl)pyrimidin-2-amine 118

2-(2-(2-(bis(tert-butoxycarbonyl)amino)pyrimidin-5-yl)-6-morpholino-9H-purin-2-yl (75 mg) was reacted with 1-(bromomethyl)-3-methoxybenzene via General Procedure C followed by Boc deprotection via General Procedure E to give 50.2 mg 118 as white solid following reverse phase purification. MS (Q1) 419.2 (M)+

Example 25 methyl 3-((2-(2-aminopyrimidin-5-yl)-6-morpholino-9H-purin-9-yl)methyl)benzoate 119

2-(2-(2-(Bis(tert-butoxycarbonyl)amino)pyrimidin-5-yl)-6-morpholino-9H-purin-2-yl (75 mg) was reacted with methyl 3-(bromomethyl)benzoate via General Procedure C followed by Boc deprotection via General Procedure E to give 27.6 mg 119 as white solid following reverse phase purification. MS (Q1) 447.2 (M)+

Example 26

3-(2-(2-aminopyrimidin-5-yl)-6-morpholino-9H-purin-9-yl)propan-1-ol 120

2-(2-(2-(bis(tert-butoxycarbonyl)amino)pyrimidin-5-yl)-6-morpholino-9H-purin-2-yl (75 mg) was reacted with 3-bromopropan-1-ol via General Procedure C followed by Boc deprotection via General Procedure E to give 19.6 mg 120 as white solid following reverse phase purification. MS (Q1) 357.2 (M)+

Example 27

2-(2-(2-aminopyrimidin-5-yl)-6-morpholino-9H-purin-9-yl)ethanol 121

2-(2-(2-(Bis(tert-butoxycarbonyl)amino)pyrimidin-5-yl)-6-morpholino-9H-purin-2-yl (75 mg) was reacted with 2-bromoethyl acetate via General Procedure C followed by Boc deprotection via General Procedure E to give 22 mg 121 as white solid following reverse phase purification. MS (Q1) 343.2 (M)+.

Example 28

1-(2-(2-(2-aminopyrimidin-5-yl)-6-morpholino-9H-purin-9-yl)acetyl)-N-methylpiperidine-4-carboxamide 122

2-(2-(2-(Tert-butoxycarbonylamino)pyrimidin-5-yl)-6-morpholino-9H-purin-9-yl)acetic acid (35 mg) was reacted with N-methylpiperidine-4-carboxamide via General Procedure F followed by Boc deprotection via General Procedure E and purified via reverse phase HPLC to give 10.3 mg 122 as a white solid. MS (Q1) 481.2 (M)+.

Example 29

2-(2-(2-aminopyrimidin-5-yl)-6-morpholino-9H-purin-9-yl)-1-(4-(methylsulfonyl)piperazin-1-yl)ethanone 123

2-(2-(2-(tert-butoxycarbonylamino)pyrimidin-5-yl)-6-morpholino-9H-purin-9-yl)acetic acid (35 mg) was reacted with 1-(methylsulfonyl)piperazine via General Procedure E followed by Boc deprotection via General Procedure D and purified via reverse phase HPLC to give 9 mg 123 as a white solid. MS (Q1) 503.2 (M)+.

Example 30

2-(2-(2-aminopyrimidin-5-yl)-6-morpholino-9H-purin-9-yl)-1-morpholinoethanone 124

2-(2-(2-(Tert-butoxycarbonylamino)pyrimidin-5-yl)-6-morpholino-9H-purin-9-yl)acetic acid (35 mg) was reacted with morpholine via General Procedure F followed by Boc deprotection via General Procedure E and purified via reverse phase HPLC to give 3.2 mg 124 as a white solid. MS (Q1) 426.2 (M)+

Example 31

2-(2-(2-aminopyrimidin-5-yl)-6-morpholino-9H-purin-9-yl)acetic acid 125

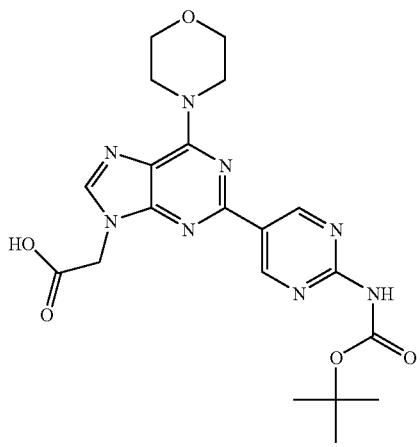

Crude 2-(2-(2-(bis(tert-butoxycarbonyl)amino)pyrimidin-5-yl)-6-morpholino-9H-purin-9-yl)acetate (240 mg) was reacted with 3 eq of lithium hydroxide in 1:1 THF/water solution. After completion, the THF was concentrated in vacuo and the water solution was acidified to pH 2 using a concentrated HCl solution. The product precipitated as a fine white solid and was filtered to yield 2-(2-(2-(tert butoxycarbonylamino)pyrimidin-5-yl)-6-morpholino-9H-purin-9-yl)acetic acid (145 mg), of which 40 mg was subjected to General Procedure E and purified via reverse phase HPLC to give 19.5 mg 125 as a white solid. MS (Q1) 357.2 (M)+

Example 32 methyl 2-(2-(2-aminopyrimidin-5-yl)-6-morpholino-9H-purin-9-yl)acetate 126

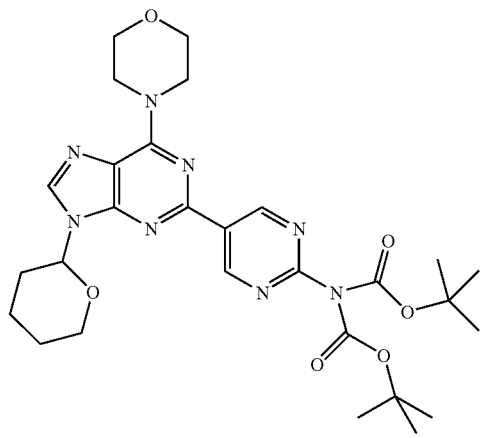

4-(2-Chloro-9-(tetrahydro-2H-pyran-2-yl)-9H-purin-6-yl)morpholine (4.05 gm) was reacted with 2-aminopyrimidine-5-boronic acid, pinacol ester via General Procedure A to give 4.75 g of 5-(6-morpholino-9-(tetrahydro-2H-pyran-2-yl)-9H-purin-2-yl)pyrimidin-2-amine which was refluxed in the presence of a catalytic amount of dimethylaminopyridine, 4 eq Boc-anhydride and 3 eq triethylamine in 60 mL of acetonitrile. Upon completion, the reaction was cooled, concentrated to dryness and purified via normal phase chromatography to yield 6.11 g of 2-(2-(2-(bis(tert-butoxycarbonyl)amino)pyrimidin-5-yl)-6-morpholino-9-(tetrahydro-2H-pyran-2-yl)-9H-purin-2-yl as a light yellow solid.

2-(2-(2-(bis(tert-butoxycarbonyl)amino)pyrimidin-5-yl)-6-morpholino-9-(tetrahydro-2H-pyran-2-yl)-9H-purin-2-yl (2 gm) was subjected to General Procedure D to selectively remove the THP protecting group and 300 mg 2-(2-(2-(bis(tert-butoxycarbonyl)amino)pyrimidin-5-yl)-6-morpholino-9H-purin-2-yl was reacted with methyl 2-bromoacetate via General Procedure C to give methyl 2-(2-(2-(bis(tert-butoxycarbonyl)amino)pyrimidin-5-yl)-6-morpholino-9H-purin-9-yl)acetate. The Boc groups of crude methyl 2-(2-(2-(bis(tert-butoxycarbonyl)amino)pyrimidin-5-yl)-6-morpholino-9H-purin-9-yl)acetate (60 mg) were removed via General Procedure E and the product purified via reverse phase HPLC to give 39 mg 126 as a white solid. MS (Q1) 371.2 (M)+

Example 33

5-(9-methyl-6-morpholino-9H-purin-2-yl)pyrimidin-2-amine 127

4-(2-Chloro-9-methyl-9H-purin-6-yl)morpholine (95 mg) was reacted with 2-aminopyrimidine-5-boronic acid, pinacol ester via General Procedure A and purified via reverse phase HPLC to give 26.1 mg of 127 as a white solid. MS (Q1) 313.2 (M)+

Example 34

5-(9-methyl-6-morpholino-9H-purin-2-yl)pyridin-2-amine 128

4-(2-Chloro-9-methyl-9H-purin-6-yl)morpholine (20 mg) was reacted with 5-(4,4,5,5-tetramethyl-1,3,2-dioxaborolan-2-yl)pyridin-2-amine via General Procedure A and purified via reverse phase HPLC to give 9.3 mg of 128 as a white solid. MS (Q1) 312.3 (M)+.

Example 35

4-(2-(1H-indazol-4-yl)-9-methyl-9H-purin-6-yl)morpholine 129

4-(2-Chloro-9-methyl-9H-purin-6-yl)morpholine (20 mg) was reacted with 4-(4,4,5,5-tetramethyl-1,3,2-dioxaborolan-2-yl)-1H-indazole via General Procedure A and purified via reverse phase HPLC to give 13.8 mg of 129 as a white solid. MS (Q1) 336.2 (M)+

Example 36

2-(2-(2-aminopyrimidin-5-yl)-9-methyl-6-morpholino-9H-purin-8-yl)propan-2-ol 130

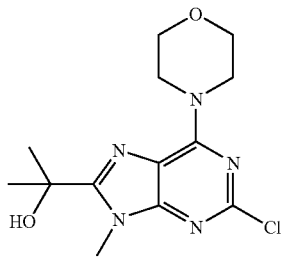

2-(2-Chloro-6-morpholino-9H-purin-8-yl)propan-2-ol (100 mg) was treated with iodomethane via General Procedure C to give crude intermediate 2-(2-chloro-9-methyl-6-morpholino-9H-purin-8-yl)propan-2-ol which was treated with 2-aminopyrimidine-5-boronic acid, pinacol ester via General Procedure A and purified via reverse phase HPLC to give 44 mg of 130 as a white solid. MS (Q1) 371.2 (M)+.

Example 37

2-(2-(6-aminopyridin-3-yl)-9-methyl-6-morpholino-9H-purin-8-yl)propan-2-ol 131

2-(2-Chloro-9-methyl-6-morpholino-9H-purin-8-yl)propan-2-ol (95 mg) was reacted with 5-(4,4,5,5-tetramethyl-1,3,2-dioxaborolan-2-yl)pyridin-2-amine via Procedure A and purified via reverse phase HPLC to give 89.3 mg of 131 as a white solid. MS (Q1) 370.3 (M)+

Example 38

2-(2-(1H-indazol-4-yl)-9-methyl-6-morpholino-9H-purin-8-yl)propan-2-ol 132

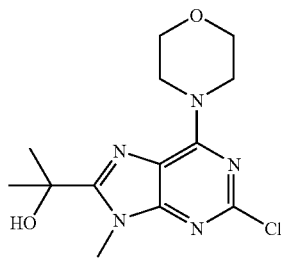

4-(2-Chloro-9-methyl-9H-purin-6-yl)morpholine (233 mg) was cooled in 5 mL of anhydrous THF to −78° C. before adding 2 eq of a 2.5 M solution of n-butyl lithium. The reaction was stirred for 1 hour at −78° C. upon which 3 eq of acetone were added. The reaction was subsequently warmed to 0° C. after 30 minutes. The reaction was quenched with water and extracted with ethyl acetate. The organic layer was concentrated to give crude 2-(2-chloro-9-methyl-6-morpholino-9H-purin-8-yl)propan-2-ol (95 mg).

Crude 2-(2-chloro-9-methyl-6-morpholino-9H-purin-8-yl)propan-2-ol was reacted with 4-(4,4,5,5-tetramethyl-1,3,2-dioxaborolan-2-yl)-1H-indazole via Procedure A and purified via reverse phase HPLC to give 56.6 mg of 132 as a white solid. MS (Q1) 394.3 (M)+

Example 39

4-(2-(1H-indazol-4-yl)-9-(2-methoxyethyl)-8-((4-(methylsulfonyl)piperazin-1-yl)methyl)-9H-purin-6-yl)morpholine 133

4-(2-chloro-8-((4-(methylsulfonyl)piperazin-1-yl)methyl)-9-(tetrahydro-2H-pyran-2-yl)-9H-purin-6-yl)morpholine (250 mg) was treated with para-toluenesulfonic acid via General Procedure D to give 4-(2-chloro-8-((4-(methylsulfonyl)piperazin-1-yl)methyl)-9H-purin-6-yl)morpholine.

4-(2-chloro-8-((4-(methylsulfonyl)piperazin-1-yl)methyl)-9H-purin-6-yl)morpholine (215 mg) was reacted with 2-bromoethylmethylether via General Procedure C to give 4-(2-chloro-9-(2-methoxyethyl)-8-((4-(methylsulfonyl)piperazin-1-yl)methyl)-9H-purin-6-yl)morpholine (207 mg) which was reacted with 4-(4,4,5,5-tetramethyl-1,3,2-dioxaborolan-2-yl)-1H-indazole via General Procedure A and purified via reverse phase HPLC to give 21.6 mg 133 as a white solid. MS (Q1) 556.3 (M)+.

Example 40

N-(4-(9-methyl-8-((4-(methylsulfonyl)piperazin-1-yl)methyl)-6-morpholino-9H-purin-2-yl)phenyl)acetamide 134

4-(2-Chloro-9-methyl-8-((4-(methylsulfonyl)piperazin-1-yl)methyl)-9H-purin-6-yl)morpholine (50 mg) was reacted with 4-acetamidophenylboronic acid via General Procedure A and purified via reverse phase HPLC to give 25.9 mg 134 as a white solid. MS (Q1) 529.3 (M)+.

Example 41

5-(9-methyl-8-((4-(methylsulfonyl)piperazin-1-yl)methyl)-6-morpholino-9H-purin-2-yl)pyridin-2-amine 135

4-(2-Chloro-9-methyl-8-((4-(methylsulfonyl)piperazin-1-yl)methyl)-9H-purin-6-yl)morpholine (50 mg) was reacted with 5-(4,4,5,5-tetramethyl-1,3,2-dioxaborolan-2-yl)pyridin-2-amine via General Procedure A and purified via reverse phase HPLC to give 29.1 mg 135 as a white solid. MS (Q1) 488.3 (M)+.

Example 42

4-(2-(2-methoxypyrimidin-5-yl)-9-methyl-8-((4-(methylsulfonyl)piperazin-1-yl)methyl)-9H-purin-6-yl)morpholine 136

4-(2-Chloro-9-methyl-8-((4-(methylsulfonyl)piperazin-1-yl)methyl)-9H-purin-6-yl)morpholine (50 mg) was reacted with 2-methoxypyrimidin-5-ylboronic acid via General Procedure A and purified via reverse phase HPLC to give 5.5 mg 136 as a white solid. MS (Q1) 504.3 (M)+.

Example 43

4-(9-methyl-8-((4-(methylsulfonyl)piperazin-1-yl)methyl)-2-(pyridin-3-yl)-9H-purin-6-yl)morpholine 137

4-(2-Chloro-9-methyl-8-((4-(methylsulfonyl)piperazin-1-yl)methyl)-9H-purin-6-yl)morpholine (50 mg) was reacted with pyridin-3-ylboronic acid via General Procedure A and purified via reverse phase HPLC to give 33.4 mg 137 as a white solid. MS (Q1) 473.3 (M)+

Example 44

4-(2-(1H-indazol-4-yl)-9-methyl-8-((4-(methylsulfonyl)piperazin-1-yl)methyl)-9H-purin-6-yl)morpholine 138

4-(2-Chloro-9H-purin-6-yl)morpholine (510 mg) was reacted with methyl iodide via General Procedure C to give 4-(2-chloro-9-methyl-9H-purin-6-yl)morpholine. 4-(2-Chloro-9-methyl-9H-purin-6-yl)morpholine (100 mg) was cooled in 1.5 mL of anhydrous THF to −78° C. before adding 2 eq of a 2.5 M solution of n-butyl lithium. The reaction was stirred for 1 hour at −78° C. upon which 3 eq of DMF were added. The reaction was subsequently warmed to 0° C. after 30 minutes. The reaction was quenched into a cold 0.25 M aqueous solution of HCl and the orange solid was filtered, collected and dried to give 48 mg crude intermediate 2-chloro-9-methyl-6-morpholino-9H-purine-8-carbaldehyde.

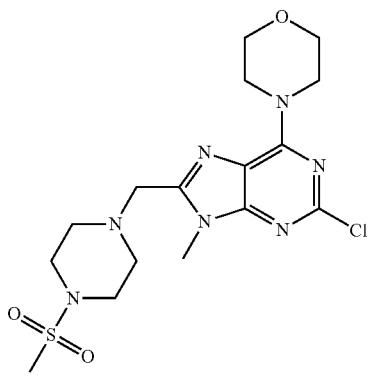

2-Chloro-9-methyl-6-morpholino-9H-purine-8-carbaldehyde was treated with 1.1 eq 1-(methylsulfonyl)piperazine, 7 eq trimethylorthoformate, 1 eq of acetic acid in 2 mL of dichloroethane for 6 hours upon which 1.1 eq of sodium triacetoxyborohydride was added to the reaction mixture. The reaction mixture was extracted with dichloromethane and water to give crude intermediate 4-(2-chloro-9-methyl-8-((4 (methylsulfonyl)piperazin-1-yl)methyl)-9H-purin-6-yl)morpholine which was then reacted with 1-(tetrahydro-2H-pyran-2-yl)-4-(4,4,5,5-tetramethyl-1,3,2-dioxaborolan-2-yl)-1H-indazole via General Procedure A and purified via reverse phase HPLC to give 41.8 mg 138 as a white solid. MS (Q1) 512.2 (M)+.

Example 45

4-(2-(2-(3-hydroxyphenyl)-6-morpholino-9H-purin-9-yl)acetyl)piperazin-2-one 139

Crude 2-(2-(3-hydroxyphenyl)-6-morpholino-9H-purin-9-yl)acetic acid (50 mg) was reacted with piperazin-2-one via General Procedure F and purified via reverse phase HPLC to give 1.9 mg of 139 as a white solid. MS (Q1) 438.2 (M)+

Example 46

2-(2-(3-hydroxyphenyl)-6-morpholino-9H-purin-9-yl)-N-methylacetamide 140

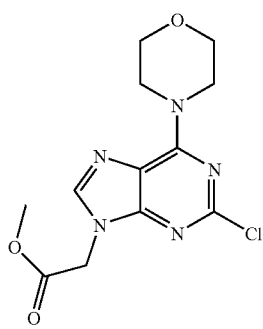

4-(2-Chloro-9H-purin-6-yl)morpholine (75 mg) was reacted with methyl 2-bromoacetate via General Procedure C. Methyl 2-(2-chloro-6-morpholino-9H-purin-9-yl)acetate was reacted with 150 mg tert-butyl-3-(4,4,5,5-tetramethyl-1,3,2-dioxaborolan-2-yl)phenyl carbonate via General Procedure A. Crude 2-(2-(3-hydroxyphenyl)-6-morpholino-9H-purin-9-yl)acetic acid (50 mg) was reacted with methylamine via General Procedure F and purified via reverse phase HPLC to give 5.6 mg of 140 as a white solid. MS (Q1) 369.2 (M)+

Example 47

3-(6-morpholino-9-(pyridin-4-ylmethyl)-9H-purin-2-yl)phenol 141

4-(2-Chloro-9H-purin-6-yl)morpholine (75 mg) was reacted with 4 (bromomethyl)pyridine via General Procedure C to give 4-(2-chloro-9-(pyridin-4-ylmethyl)-9H-purin-6-yl)morpholine which was reacted with 150 mg tert-butyl-3-(4,4,5,5-tetramethyl-1,3,2-dioxaborolan-2-yl)phenyl carbonate via General Procedure A and purified via reverse phase HPLC to give 28.1 mg of 141 as a white solid. MS (Q1) 389.2 (M)+

Example 48

3-(9-(4-fluorobenzyl)-6-morpholino-9H-purin-2-yl)phenol 142

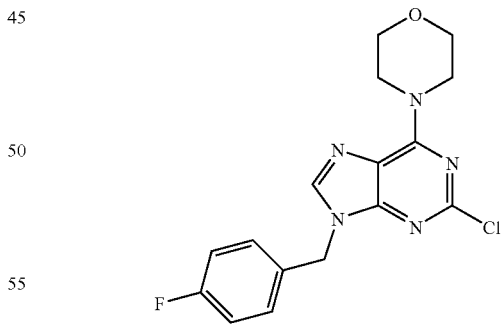

4-(2-Chloro-9H-purin-6-yl)morpholine (75 mg) was reacted with 1-(bromomethyl)-4-fluorobenzene via General Procedure C to give 4-(2-chloro-9-(4-fluorobenzyl)-9H-purin-6-yl)morpholine which was reacted with 150 mg tert-butyl-3-(4,4,5,5-tetramethyl-1,3,2-dioxaborolan-2-yl)phenyl carbonate via General Procedure A and purified via reverse phase HPLC to give 50 mg of 142 as a white solid. MS (Q1) 406.2 (M)+.

Example 49

3-(9-benzyl-6-morpholino-9H-purin-2-yl)phenol 143

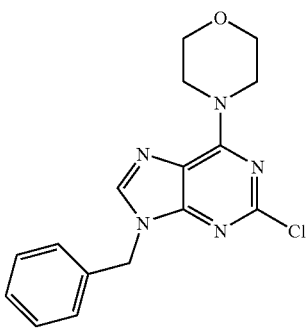

4-(2-Chloro-9H-purin-6-yl)morpholine (75 mg) was reacted with (bromomethyl)benzene via General Procedure C to give 4-(9-benzyl-2-chloro-9H-purin-6-yl)morpholine which was reacted with 150 mg tert-butyl-3-(4,4,5,5-tetramethyl-1,3,2-dioxaborolan-2-yl)phenyl carbonate via General Procedure A and purified via reverse phase HPLC to give 92.2 mg of 143 as a white solid. MS (Q1) 388.2 (M)+

Example 50

3-(9-(2-hydroxyethyl)-6-morpholino-9H-purin-2-yl)phenol 144

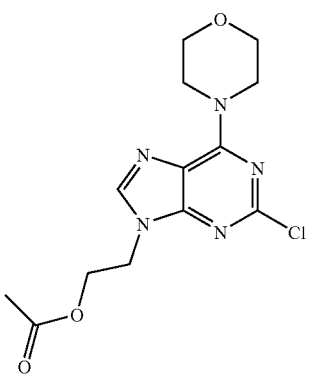

4-(2-Chloro-9H-purin-6-yl)morpholine (75 mg) was reacted with 2-bromoethyl acetate via General Procedure C to give 2-(2-chloro-6-morpholino-9H-purin-9-yl)ethyl acetate which was reacted with 150 mg tert-butyl-3-(4,4,5,5-tetramethyl-1,3,2-dioxaborolan-2-yl)phenyl carbonate via General Procedure A and purified via reverse phase HPLC to give 59.4 mg of 144 as a white solid. MS (Q1) 342.2 (M)+

Example 51

3-(9-isobutyl-6-morpholino-9H-purin-2-yl)phenol 145

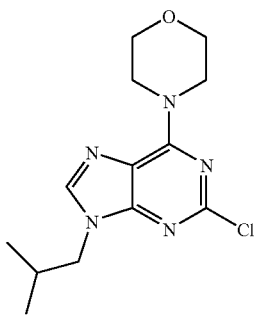

4-(2-Chloro-9H-purin-6-yl)morpholine (75 mg) was reacted with 1-iodo-2-methylpropane via General Procedure C. 4-(2-Chloro-9-isobutyl-9H-purin-6-yl)morpholine was reacted with 150 mg tert-butyl-3-(4,4,5,5-tetramethyl-1,3,2-dioxaborolan-2-yl)phenyl carbonate via General Procedure A and purified via reverse phase HPLC to give 62.6 mg of 145 as a white solid. MS (Q1) 354.2 (M)+

Example 52 p110α (alpha) PI3K Binding Assay

Binding Assays: Initial polarization experiments were performed on an Analyst HT® 96-384 (Molecular Devices Corp, Sunnyvale, Calif.). Samples for fluorescence polarization affinity measurements were prepared by addition of 1:3 serial dilutions of p110 alpha PI3K (Upstate Cell Signaling Solutions, Charlottesville, Va.) starting at a final concentration of 20 ug/mL in polarization buffer (10 mM Tris pH 7.5, 50 mM NaCl, 4 mM $MgCl_2$, 0.05% Chaps, and 1 mM DTT) to 10 mM $PIP_2$ (Echelon-Inc., Salt Lake City, Utah.) final concentration. After an incubation time of 30 minutes at room temperature, the reactions were stopped by the addition of GRP-1 and PIP3-TAMRA probe (Echelon-Inc., Salt Lake City, Utah.) 100 nM and 5 nM final concentrations respectively. Read with standard cut-off filters for the rhodamine fluorophore ($\lambda ex$=530 nm; $\lambda em$=590 nm) in 384-well black low volume ProxiPlate™ (PerkinElmer, Wellesley, Mass.) Fluorescence polarization values were plotted as a function of the protein concentration, and the $EC_{50}$ values were obtained by fitting the data to a 4-parameter equation using KaleidaGraph™ software (Synergy software, Reading, Pa.). This experiment also establishes the appropriate protein concentration to use in subsequent competition experiments with inhibitors.

Inhibitor $IC_{50}$ values were determined by addition of the 0.04 mg/mL p110 alpha PI3K (final concentration) combined with $PIP_2$ (10 mM final concentration) to wells containing 1:3 serial dilutions of the antagonists in a final concentration of 25 mM ATP (Cell Signaling Technology, Inc., Danvers, Mass.) in the polarization buffer. After an incubation time of 30 minutes at room temperature, the reactions were stopped by the addition of GRP-1 and PIP3-TAMRA probe (Echelon-Inc., Salt Lake City, Utah.) 100 nM and 5 nM final concentrations respectively. Read with standard cut-off filters for the rhodamine fluorophore ($\lambda ex$=530 nm; $\lambda em$=590 nm) in 384-well black low volume ProxiPlate™ (PerkinElmer, Wellesley, Mass.) Fluorescence polarization values were plotted as a function of the antagonist concentration, and the $IC_{50}$ values were obtained by fitting the data to a 4-parameter equation in MDL® Assay Explorer® software (MDL, San Ramon, Calif.).

Alternatively, inhibition of PI3K was determined in a radiometric assay using purified, recombinant enzyme and ATP at a concentration of 1 uM. The Formula I compound was serially diluted in 100% DMSO. The kinase reaction was incubated for 1 h at room temperature, and the reaction was terminated by the addition of PBS. $IC_{50}$ values were subsequently determined using sigmoidal dose-response curve fit (variable slope).

Example 53

In Vitro Cell Proliferation Assay

Efficacy of Formula I compounds were measured by a cell proliferation assay employing the following protocol (Promega Corp. Technical Bulletin TB288; Mendoza et al (2002) Cancer Res. 62:5485-5488):

1. An aliquot of 100 μl of cell culture containing about $10^4$ cells (PC3, Detroit562, or MDAMB361.1) in medium was deposited in each well of a 384-well, opaque-walled plate.

2. Control wells were prepared containing medium and without cells.

3. The compound was added to the experimental wells and incubated for 3-5 days.

4. The plates were equilibrated to room temperature for approximately 30 minutes.

5. A volume of CellTiter-Glo® Reagent equal to the volume of cell culture medium present in each well was added.

6. The contents were mixed for 2 minutes on an orbital shaker to induce cell lysis.

7. The plate was incubated at room temperature for 10 minutes to stabilize the luminescence signal.

8. Luminescence was recorded and reported in graphs as RLU=relative luminescence units.

Alternatively, cells were seeded at optimal density in a 96 well plate and incubated for 4 days in the presence of test compound. Alamar Blue™ was subsequently added to the assay medium, and cells were incubated for 6 h before reading at 544 nm excitation, 590 nm emission. $EC_{50}$ values were calculated using a sigmoidal dose response curve fit.

Example 54

Caco-2 Permeability

Caco-2 cells are seeded onto Millipore® Multiscreen® plates at $1\times10^5$ cells/cm$^2$, and cultured for 20 days. Assessment of compound permeability is subsequently conducted. The compounds are applied to the apical surface (A) of cell monolayers and compound permeation into the basolateral (B) compartment was measured. This is performed in the reverse direction (B-A) to investigate active transport. A permeability coefficient value, $P_{app}$, for each compound, a measure of the rate of permeation of the compound across the membrane, is calculated. Compounds are grouped into low ($P_{app}</=1.0\times10^6$ cm/s) or high ($P_{app}>/=1.0\times10^6$ cm/s) absorption potential based on comparison with control compounds with established human absorption.

For assessment of a compound's ability to undergo active efflux, the ratio of basolateral (B) to apical (A) transport compared with A to B was determined. Values of B-A/A-B>/= 1.0 indicate the occurrence of active cellular efflux.

Example 55

Hepatocyte Clearance

Suspensions of cryopreserved human hepatocytes are used. Incubations are performed at compound concentration of 1 mM or 3 μM at a cell density of $0.5\times10^6$ viable cells/mL. The final DMSO concentration in the incubation is about 0.25%. Control incubations are also performed in the absence of cells to reveal any non-enzymatic degradation. Duplicate samples (50 μL) are removed from the incubation mixture at 0, 5, 10, 20, 40 and 60 minutes (control sample at 60 minutes only) and added to MeOH—containing internal standard (100 μL)—to terminate the reaction. Tolbutamide, 7-hydroxycoumarin, and testosterone may be used as control compounds. Samples are centrifuged and the supernatants at each time point pooled for analysis by LC-MSMS. From a plot of ln peak area ratio (parent compound peak area/internal standard peak area) against time, intrinsic clearance ($CL_{int}$) is calculated as follows: $CL_{int}$ (μl/min/million cells)=V×k, where k is the elimination rate constant, obtained from the gradient of ln concentration plotted against time; V is a volume term derived from the incubation volume and is expressed as uL $10^6$ cells$^{-1}$.

Example 56

Cytochrome P450 Inhibition

Formula I compounds may be screened against CYP450 targets (1A2, 2C9, 2C19, 2D6, 3A4) at about 10 concentrations in duplicate, with a top concentration of about 100 uM. Standard inhibitors (furafylline, sulfaphenazole, tranylcypromine, quinidine, ketoconazole) may be used as controls. Plates may be read using a BMG LabTechnologies PolarStar in fluorescence mode.

Example 57

Cytochrome P450 Induction

Freshly isolated human hepatocytes from a single donor may be cultured for about 48 h prior to addition of Formula I compound at three concentrations and incubated for 72 h. Probe substrates for CYP3A4 and CYP1A2 are added for 30 minutes and 1 h before the end of the incubation. At 72 h, cells and media are removed and the extent of metabolism of each probe substrate quantified by LC-MS/MS. The experiment is controlled by using inducers of the individual P450s incubated at one concentration in triplicate.

Example 58

Plasma Protein Binding

Solutions of Formula I compound (5 um, 0.5% final DMSO concentration) are prepared in buffer and 10% plasma (v/v in buffer). A 96 well HT dialysis plate is assembled so that each well is divided in two by a semi-permeable cellulose membrane. The buffer solution is added to one side of the membrane and the plasma solution to the other side; incubations are then conducted at 37° C. over 2 h in triplicate. The cells are subsequently emptied, and the solutions for each batch of compounds are combined into two groups (plasma-free and plasma-containing) then analyzed by LC-MSMS using two sets of calibration standards for plasma-free (6 points) and plasma-containing solutions (7 points). The fraction unbound value for the compound is calculated.

Example 59 hERG Channel Blockage

Formula I compounds are evaluated for ability to modulate rubidium efflux from HEK-294 cells stably expressing hERG potassium channels using established flux methodology. Cells are prepared in medium containing RbCl, plated into 96-well plates and grown overnight to form monolayers. The efflux experiment is initiated by aspirating the media and washing each well with 3×100 μL of pre-incubation buffer (containing low [K+]) at room temperature. Following the final aspiration, 50 μL of working stock (2×) compound is added to each well and incubated at room temperature for 10 minutes. 50 μL of stimulation buffer (containing high [K+]) is then added to each well giving the final test compound concentrations. Cell plates are then incubated at room temperature for a further 10 minutes. 80 μL of supernatant from each well is then transferred to equivalent wells of a 96-well plate and analyzed via atomic emission spectroscopy. The compound is screened as 10 pt duplicate $IC_{50}$ curves, n=2, from a top concentration of 100 μM.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A compound having the structure:

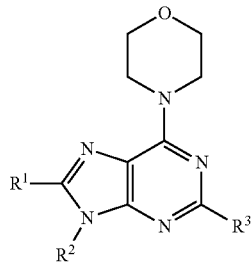

and stereoisomers, geometric isomers, tautomers, or pharmaceutically acceptable salts thereof, wherein:

$R^1$ is selected from H, $C_1$-$C_{12}$ alkyl, and —($C_1$-$C_{12}$ alkylene)-($C_2$-$C_{20}$ heterocyclyl), where alkyl, alkylene, and heterocyclyl are optionally substituted with one or more groups independently selected from F, Cl, Br, I, —$CH_3$, —$CH_2OH$, —CN, —$CF_3$, —$CO_2H$, —$COCH_3$, —$CO_2CH_3$, —$CONH_2$, —$CONHCH_3$, —$CON(CH_3)_2$, —$NO_2$, —$NH_2$, —$NHCH_3$, —$NHCOCH_3$, —$NHS(O)_2CH_3$, —OH, —$OCH_3$, —$S(O)_2N(CH_3)_2$, —$SCH_3$, —$CH_2OCH_3$, and —$S(O)_2CH_3$, $R^2$ is selected from $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2OH$, —CN, —$CF_3$, —$CO_2H$, —$COCH_3$, —$CO_2CH_3$, —$CONH_2$, —$CONHCH_3$, —$CON(CH_3)_2$, —$NO_2$, —$NH_2$, —$NHCH_3$, —$NHCOCH_3$, —$NHS(O)_2CH_3$, —OH, —$OCH_3$, —$S(O)_2N(CH_3)_2$, —$SCH_3$, —$CH_2OCH_3$, and —$S(O)_2CH_3$; and $R^3$ is a monocyclic heteroaryl selected from:

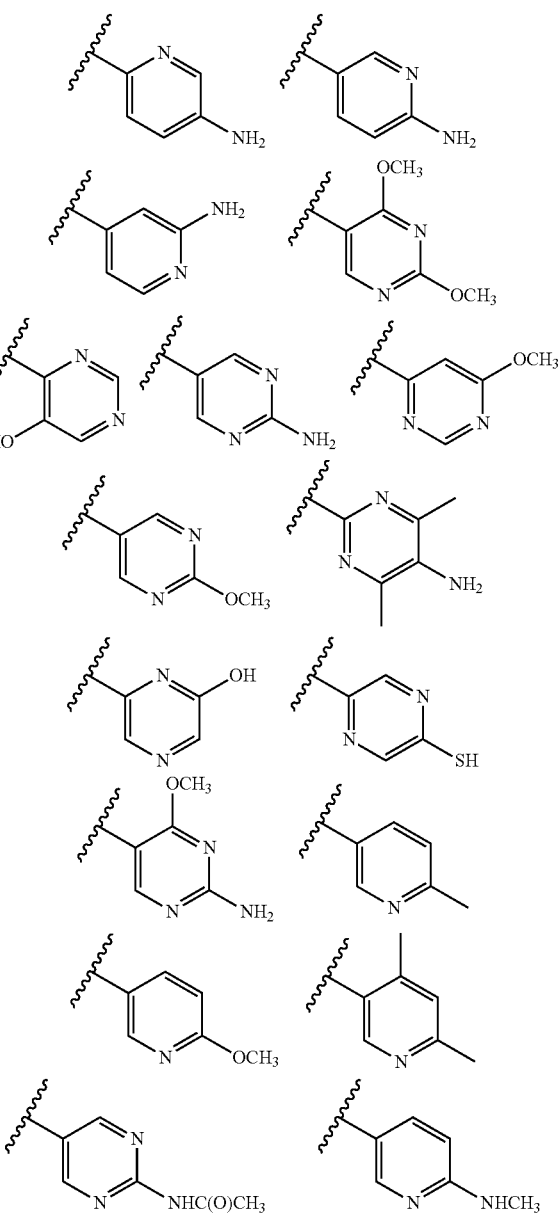

-continued

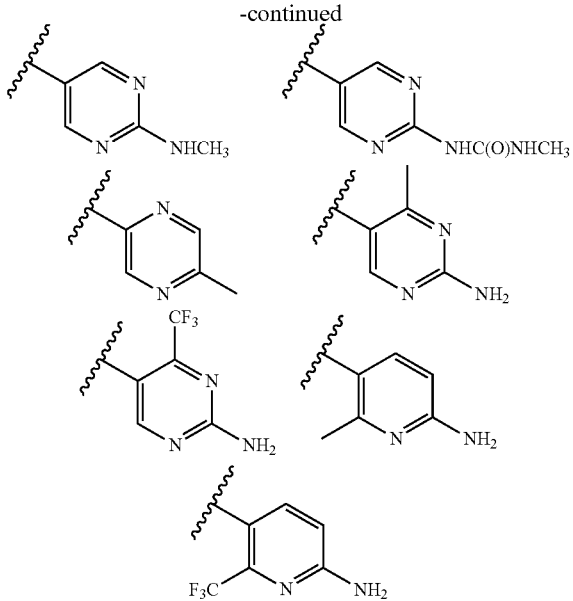

where the wavy line indicates the site of attachment.

2. The compound of claim 1 wherein $R^1$ is selected from $CH_3$, $-CH_2CH_3$, $-CH_2CH_2CH_3$, $-CH(CH_3)_2$, $-CH_2CH_2CH_2CH_3$, $-CH_2CH(CH_3)_2$, $-C(CH_3)_2OH$, $-CH_2CH_2OH$, and $-CH_2CH_2CH_2OH$.

3. The compound of claim 1 wherein $R^1$ is $C_1$-$C_{12}$ alkyl substituted with one or more —F.

4. The compound of claim 1 wherein $R^1$ is —($C_1$-$C_{12}$ alkylene)-($C_2$-$C_{20}$ heterocyclyl).

5. The compound of claim 4 wherein $R^1$ is —$CH_2$-(piperazin-1-yl) where piperazin-1-yl is optionally substituted.

6. The compound of claim 5 wherein $R^1$ is —$CH_2$-(4-(methylsulfonyl)piperazin-1-yl).

7. The compound of claim 1 wherein $R^2$ is selected from $CH_3$, $-CH_2CH_3$, $-CH_2CH_2CH_3$, $-CH(CH_3)_2$, $-CH_2CH_2CH_2CH_3$, and $-CH_2CH(CH_3)_2$.

8. The compound of claim 1 wherein $R^2$ is $C_1$-$C_{12}$ alkyl substituted with one or more —F.

9. The compound of claim 1 wherein $R^2$ is —($C_1$-$C_{12}$ alkylene)-($C_2$-$C_{20}$ heterocyclyl).

10. The compound of claim 9 wherein $R^2$ is —$CH_2$-(piperazin-1-yl) where piperazin-1-yl is optionally substituted.

11. The compound of claim 10 wherein $R^2$ is —$CH_2$-(4-(methylsulfonyl)piperazin-1-yl).

12. The compound of claim 1 selected from:
2-(2-(2-amino-4-methylpyrimidin-5-yl)-9-(2-hydroxyethyl)-6-morpholino-9H-purin-8-yl)propan-2-ol;
2-(2-(2-aminopyrimidin-5-yl)-9-butyl-6-morpholino-9H-purin-8-yl)propan-2-ol;
2-(2-(2-aminopyrimidin-5-yl)-6-morpholino-9-propyl-9H-purin-8-yl)propan-2-ol;
3-(2-(2-aminopyrimidin-5-yl)-8-(2-hydroxypropan-2-yl)-6-morpholino-9H-purin-9-yl)propan-1-ol;
2-(2-(2-aminopyrimidin-5-yl)-9-(2-hydroxyethyl)-6-morpholino-9H-purin-8-yl)propan-2-ol;
1-(4-((2-(2-aminopyrimidin-5-yl)-6-morpholino-9H-purin-9-yl)methyl)piperidin-1-yl)ethanone;
1-(3-((2-(2-aminopyrimidin-5-yl)-6-morpholino-9H-purin-9-yl)methyl)pyrrolidin-1-yl)ethanone;
(R)-3-(2-(2-aminopyrimidin-5-yl)-6-morpholino-9H-purin-9-yl)-1-(3-hydroxypyrrolidin-1-yl)propan-1-one;
(S)-3-(2-(2-aminopyrimidin-5-yl)-6-morpholino-9H-purin-9-yl)-1-(3-hydroxypyrrolidin-1-yl)propan-1-one;
1-(3-(2-(2-aminopyrimidin-5-yl)-6-morpholino-9H-purin-9-yl)propanoyl)-N-methylpiperidine-4-carboxamide;
3-(2-(2-aminopyrimidin-5-yl)-6-morpholino-9H-purin-9-yl)-1-(4-(methylsulfonyl)piperazin-1-yl)propan-1-one;
3-(2-(2-aminopyrimidin-5-yl)-6-morpholino-9H-purin-9-yl)-1-morpholinopropan-1-one;
3-(2-(2-aminopyrimidin-5-yl)-6-morpholino-9H-purin-9-yl)propanoic acid;
5-(9-(4-(methylsulfonyl)benzyl)-6-morpholino-9H-purin-2-yl)pyrimidin-2-amine;
methyl 4-((2-(2-aminopyrimidin-5-yl)-6-morpholino-9H-purin-9-yl)methyl)benzoate;
5-(6-morpholino-9-(2-morpholinoethyl)-9H-purin-2-yl)pyrimidin-2-amine;
5-(9-(3-methoxybenzyl)-6-morpholino-9H-purin-2-yl)pyrimidin-2-amine;
methyl 3-((2-(2-aminopyrimidin-5-yl)-6-morpholino-9H-purin-9-yl)methyl)benzoate;
3-(2-(2-aminopyrimidin-5-yl)-6-morpholino-9H-purin-9-yl)propan-1-ol;
2-(2-(2-aminopyrimidin-5-yl)-6-morpholino-9H-purin-9-yl)ethanol;
1-(2-(2-(2-aminopyrimidin-5-yl)-6-morpholino-9H-purin-9-yl)acetyl)-N-methylpiperidine-4-carboxamide;
2-(2-(2-aminopyrimidin-5-yl)-6-morpholino-9H-purin-9-yl)-1-(4-(methylsulfonyl)piperazin-1-yl)ethanone;
2-(2-(2-aminopyrimidin-5-yl)-6-morpholino-9H-purin-9-yl)-1-morpholinoethanone;
2-(2-(2-aminopyrimidin-5-yl)-6-morpholino-9H-purin-9-yl)acetic acid;
methyl 2-(2-(2-aminopyrimidin-5-yl)-6-morpholino-9H-purin-9-yl)acetate;
5-(9-methyl-6-morpholino-9H-purin-2-yl)pyrimidin-2-amine;
5-(9-methyl-6-morpholino-9H-purin-2-yl)pyridin-2-amine;
2-(2-(2-aminopyrimidin-5-yl)-9-methyl-6-morpholino-9H-purin-8-yl)propan-2-ol;
2-(2-(6-aminopyridin-3-yl)-9-methyl-6-morpholino-9H-purin-8-yl)propan-2-ol;
5-(9-methyl-8-((4-(methylsulfonyl)piperazin-1-yl)methyl)-6-morpholino-9H-purin-2-yl)pyridin-2-amine;
4-(2-(2-methoxypyrimidin-5-yl)-9-methyl-8-((4-(methylsulfonyl)piperazin-1-yl)methyl)-9H-purin-6-yl)morpholine;
4-(9-methyl-8-((4-(methylsulfonyl)piperazin-1-yl)methyl)-2-(pyridin-3-yl)-9H-purin-6-yl)morpholine;
5-(8-((4-(dimethylamino)piperidin-1-yl)methyl)-9-ethyl-6-morpholino-9H-purin-2-yl)pyrimidin-2-amine;
5-(8-((4-(azetidin-1-yl)piperidin-1-yl)methyl)-9-ethyl-6-morpholino-9H-purin-2-yl)pyrimidin-2-amine;
5-(8-((4-(azetidin-1-yl)piperidin-1-yl)methyl)-9-ethyl-6-morpholino-9H-purin-2-yl)-4-methylpyrimidin-2-amine;
2-(4-((2-(2-amino-4-methylpyrimidin-5-yl)-9-ethyl-6-morpholino-9H-purin-8-yl)methyl)piperazin-1-yl)-2-methylpropanamide;
5-(8-((4-(dimethylamino)piperidin-1-yl)methyl)-9-ethyl-6-morpholino-9H-purin-2-yl)-4-methylpyrimidin-2-amine;
5-(8-(1,4'-bipiperidin-1'-ylmethyl)-9-ethyl-6-morpholino-9H-purin-2-yl)-4-methylpyrimidin-2-amine;
5-(8-(1,4'-bipiperidin-1'-ylmethyl)-9-ethyl-6-morpholino-9H-purin-2-yl)pyrimidin-2-amine;

5-(9-ethyl-6-morpholino-8-((4-morpholinopiperidin-1-yl)methyl)-9H-purin-2-yl)-4-methylpyrimidin-2-amine;

5-(9-ethyl-6-morpholino-8((4-morpholinopiperidin-1-yl)methyl)-9H-purin-2-yl)pyrimidin-2-amine;

N-(1-((2-(2-amino-4-methylpyrimidin-5-yl)-9-ethyl-6-morpholino-9H-purin-8-yl)methyl)piperidin-4-yl)-N-methylmethanesulfonamide; and N-(1-((2-(2-aminopyrimidin-5-yl)-9-ethyl-6-morpholino-9H-purin-8-yl)methyl)piperidin-4-yl)-N-methylmethanesulfonamide.

13. A pharmaceutical composition comprised of a compound of claim 1 and a pharmaceutically acceptable carrier, glidant, diluent, or excipient.

\* \* \* \* \*

UNITED STATES PATENT AND TRADEMARK OFFICE
CERTIFICATE OF CORRECTION

| | | |
|---|---|---|
| PATENT NO. | : 8,158,624 B2 | Page 1 of 1 |
| APPLICATION NO. | : 12/474613 | |
| DATED | : April 17, 2012 | |
| INVENTOR(S) | : Georgette Castanedo et al. | |

It is certified that error appears in the above-identified patent and that said Letters Patent is hereby corrected as shown below:

Title Page, Item (73) Assignee should read:

--Genentech, Inc., South San Francisco, CA (US)--

Signed and Sealed this
Third Day of July, 2012

David J. Kappos
*Director of the United States Patent and Trademark Office*